(12) United States Patent
Levy et al.

(10) Patent No.: US 9,439,973 B2
(45) Date of Patent: Sep. 13, 2016

(54) TRANSFERRIN RECEPTOR APTAMERS AND APTAMER-TARGETED DELIVERY

(71) Applicant: ALBERT EINSTEIN COLLEGE OF MEDICINE OF YESHIVA UNIVERSITY, Bronx, NY (US)

(72) Inventors: Matthew Levy, New Rochelle, NY (US); Keith Everett Maier, Bronx, NY (US); Samantha E. Wilner, Holden, MA (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 193 days.

(21) Appl. No.: 14/396,102

(22) PCT Filed: Apr. 24, 2013

(86) PCT No.: PCT/US2013/038006
§ 371 (c)(1),
(2) Date: Oct. 22, 2014

(87) PCT Pub. No.: WO2013/163303
PCT Pub. Date: Oct. 31, 2013

(65) Prior Publication Data
US 2015/0125516 A1    May 7, 2015

Related U.S. Application Data

(60) Provisional application No. 61/638,244, filed on Apr. 25, 2012.

(51) Int. Cl.
| | | |
|---|---|---|
| *A61K 48/00* | (2006.01) |
| *C07H 21/02* | (2006.01) |
| *C12Q 1/68* | (2006.01) |
| *C12N 15/11* | (2006.01) |
| *A61K 47/48* | (2006.01) |
| *C12N 7/00* | (2006.01) |
| *C12N 15/115* | (2010.01) |
| *C12N 15/113* | (2010.01) |
| *A61K 31/7105* | (2006.01) |

(52) U.S. Cl.
CPC ..... *A61K 47/48092* (2013.01); *A61K 31/7105* (2013.01); *C12N 7/00* (2013.01); *C12N 15/115* (2013.01); *C12N 15/1138* (2013.01); *C12N 2310/14* (2013.01); *C12N 2310/16* (2013.01); *C12N 2310/321* (2013.01); *C12N 2310/3521* (2013.01); *C12N 2310/531* (2013.01); *C12N 2760/10011* (2013.01)

(58) Field of Classification Search
CPC .................................................. C12N 15/115
See application file for complete search history.

(56) References Cited

U.S. PATENT DOCUMENTS

| 6,812,339 B1 | 11/2004 | Venter et al. |
| 2008/0008996 A1 | 1/2008 | Byrum |
| 2010/0261781 A1 | 10/2010 | Gmeiner |

FOREIGN PATENT DOCUMENTS

WO    2011142798 A2    11/2011

OTHER PUBLICATIONS

PCT International Search Report and Written Opinion, dated Dec. 6, 2013 in connection with PCT International Application No. PCT/US2013/38006, 13 pages.
Willis M C et al., entitled "Liposome-Anchored Vascular Endothelial Growth Factor Aptamers," Bioconjugate Chem., 1998, 9, 573-582.
Kang H et al., entitled "A liposome-based nanostructure for aptamer directed delivery," Chem. Commun., 2010, 46, 249-251, with Supporting Information, 6 pages.

*Primary Examiner* — Dana Shin
(74) *Attorney, Agent, or Firm* — Amster, Rothstein & Ebenstein LLP

(57) ABSTRACT

Aptamers targeted to a human transferrin receptor which do not compete with transferrin for binding are provided. Compositions and methods for aptamer-targeted liposomal drug delivery are also provided.

Figures 1A, 1B, 1C:
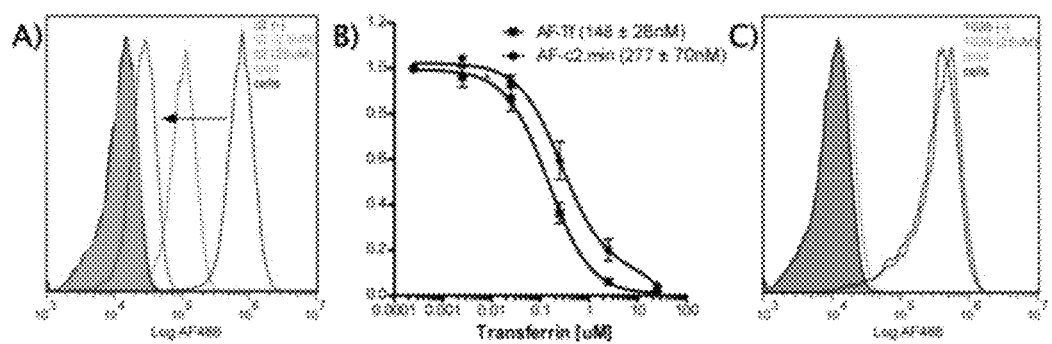

17 Claims, 8 Drawing Sheets
(7 of 8 Drawing Sheet(s) Filed in Color)

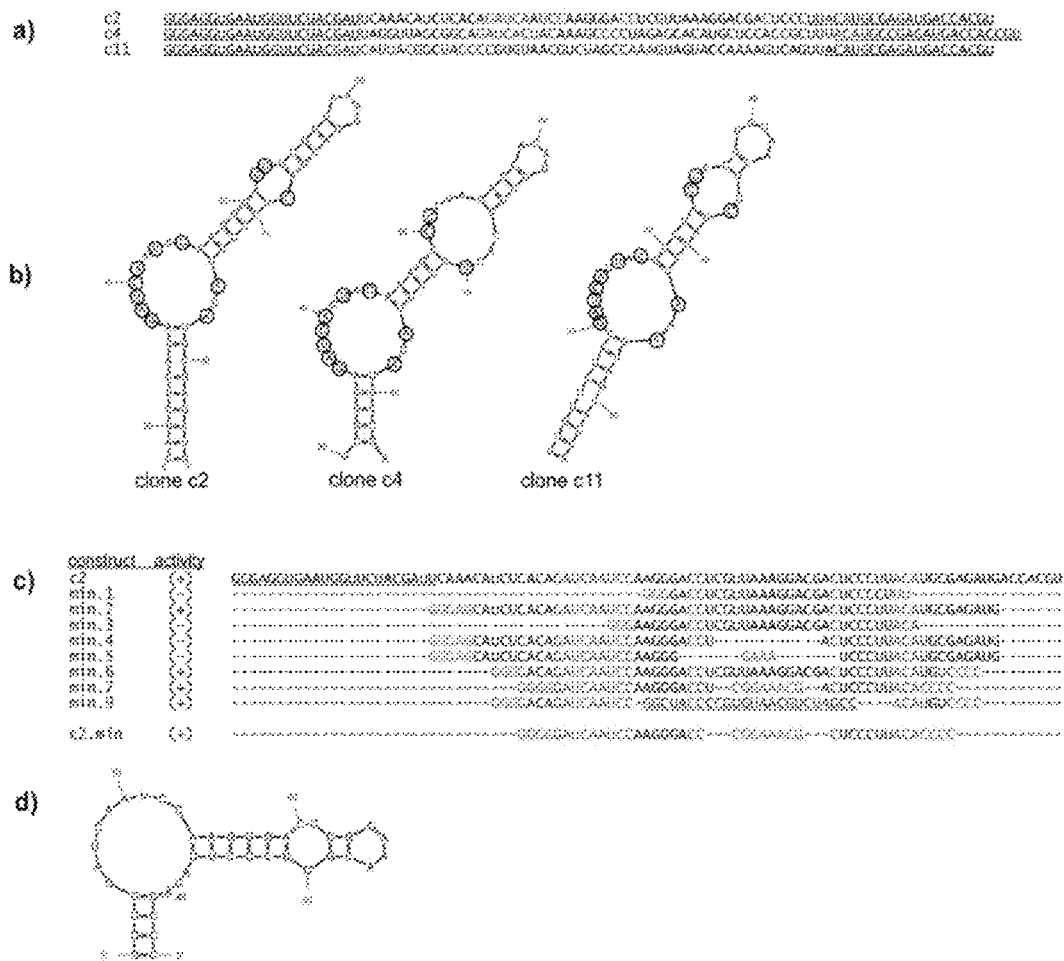
Fig. 3(A)-(D)

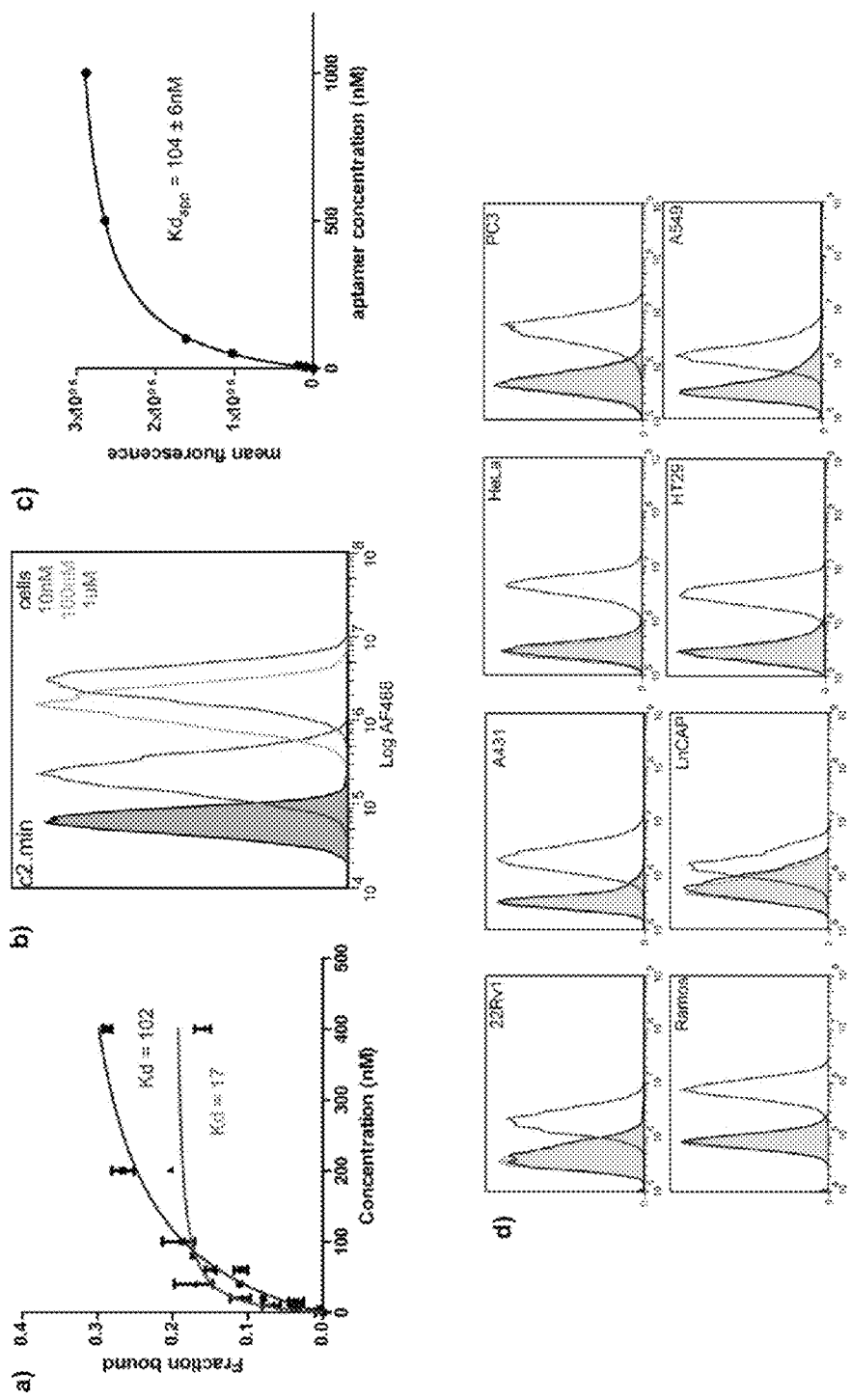
Fig. 4(A)-(D)

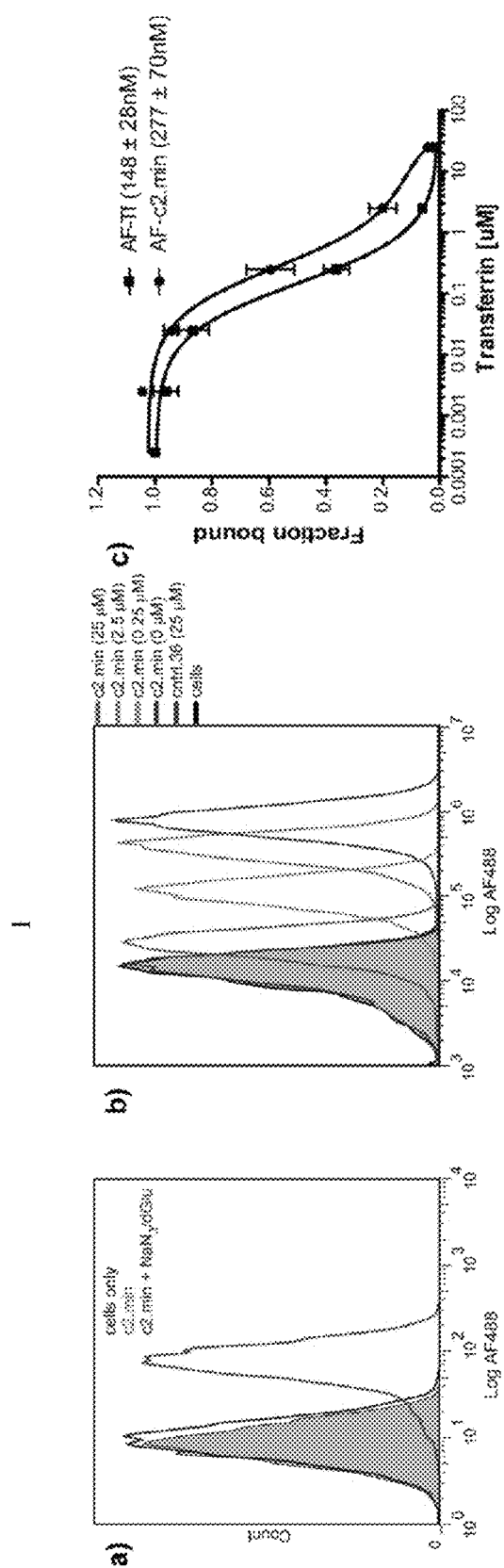
Fig. 5(A)-(C)

TRANSFERRIN RECEPTOR APTAMERS AND APTAMER-TARGETED DELIVERY

CROSS-REFERENCE TO RELATED APPLICATIONS

This application is a U.S. national stage entry under 35 U.S.C. §371 of PCT International Patent Application No. PCT/US2013/038006, filed Apr. 24, 2013, which claims benefit of U.S. Provisional Application No. 61/638,244, filed Apr. 25, 2012, the contents of each of which are incorporated herein by reference into the subject application.

BACKGROUND OF THE INVENTION

Throughout this application various publications, patents, patent application publications and books are referred to. Full citations for these may be found at the end of the specification. The disclosures of these publications, patents, patent application publications and books are hereby incorporated by reference in their entirety into the subject application to more fully describe the art to which the subject invention pertains.

From laboratory to clinic, directing therapeutics to specific sites (cells, tumors, tissues) and ensuring that the delivered agents will be active only at the desired sites remains a daunting challenge. Targeting is a particularly critical issue in cancer therapy because of the undesirable side effects of chemotherapeutic agents, many of which can also be toxic to normal cells.

The transferrin receptor, CD71 (TfR), is one of the mostly widely targeted receptors for development of targeted cancer diagnostics and therapeutics [1]. This type II transmembrane glycoprotein is responsible for cellular iron transport and is found at low levels on the surface of many normal cell types. However, the receptor is highly expressed on cells with increased proliferation rates. In particular, increased expression is observed across a wide range of cancer cells where increased expression is associated with poor prognosis [2]. Perhaps most interestingly, the receptor is also expressed at high levels on the blood brain barrier where it has been shown to be a route for ferrying cargoes across the blood brain barrier [3].

The natural ligand of this receptor, transferrin, has been used extensively for the generation of numerous targeted drug delivery strategies including the development of targeted toxins, some of which have gotten as far as clinical trials [4-7]. Aside from anti-integrin binding RGD peptides, transferrin is perhaps the most commonly used targeting ligand for functionalizing nanoparticles for nanoparticle-based diagnostics and therapeutics [8, 9]. Nanoparticles in and of themselves have a tendency to accumulate in the fenestrations of tumors through a phenomenon known as the enhanced permeability and retention (EPR) effect [10]; however, greater gains, in particular extravasation and tissue penetration, can be achieved by including targeting ligands on the surface of nanoparticles. Specifically, transferrin has previously been shown to enhance the effect of nanoparticle based siRNA delivery in vivo [11].

In addition to the natural ligand, transferrin, a variety of antibodies [1] and even peptides [12] have been identified which target the transferrin receptor. More recently, Chen et al. reported the development of both RNA as well as DNA aptamers which target the murine transferrin receptor and demonstrated that a DNA aptamer-alpha-l-iduronidase conjugate taken up by alpha-L-iduronidase-deficient mouse fibroblasts cells were transported to lysosomes where they alleviated glycosaminoglycan accumulation [13]. The selected aptamers were specific for the mouse receptor but were, unfortunately, composed of natural nucleotides rendering them highly susceptible to degradation by serum nucleases and thus limiting their utility.

The present invention provides aptamers are engineered to target specific cells and methods of targeted delivery using aptamers.

SUMMARY OF THE INVENTION

An isolated ribonucleic acid aptamer is provided comprising SEQ ID NO:1, 2, 3, 5, 10, 51 or 52-60.

Also provided is an isolated ribonucleic acid aptamer of 60 bases or less which binds a human transferrin receptor but which does not compete with human transferrin for binding to the human transferrin receptor.

Also provided is a composition comprising any of the aptamers described herein. In an embodiment, the composition comprises a pharmaceutically acceptable carrier.

Also provided is a composition, comprising any of the aptamers described herein conjugated to one of an oligonucleotide, a small organic molecule of less than 2000 daltons, a liposome or a nanoparticle.

Also provided is a composition, comprising a ribonucleic acid aptamer directed to a receptor, which aptamer is attached to a nanoparticle or liposome.

Also provided is a method of delivering a molecular entity to a receptor-expressing cell in a subject comprising administering to the subject any of the compositions described herein, wherein the molecular entity is conjugated to the aptamer or contained in a liposome attached to the aptamer, so as to thereby deliver the molecular entity to a receptor-expressing cell.

This invention provides a method of inhibiting a New World arenavirus from infecting a cell comprising contacting the cell with an amount of a ribonucleic acid aptamer, or an oliogimer thereof, which binds a transferrin receptor effective to inhibit a New World arenavirus from infecting a cell.

This invention also provides a method of treating a subject exposed to a New World arenavirus comprising administering to the subject an amount of a ribonucleic acid aptamer, or an oligomer thereof, which binds a transferrin receptor effective to inhibit a New World arenavirus from infecting a cell and treat a subject exposed to a New World arenavirus.

Additional objects of the invention will be apparent from the description which follows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A-1C. (A) Binding and uptake of AF488-labeled anti-TfR aptamer c2 by Jurkat cells in the presence of increasing concentrations of free transferrin. 100 nM aptamer was incubated with cells for 1 hr in media. The concentration of free transferrin added to the media is indicated in parentheses. Cells analyzed by flow cytometry. (B) Determination of the IC50 for binding and uptake of AF488-c2 and DY488-Tf. Experimental conditions were as in (A). (C) Binding and uptake of AF488-labeled anti TfR aptamer 1036 by Jurkat cells in the presence of increasing concentrations of free transferrin. 100 nM aptamer was incubated with cells for 1 hr in media. The concentration of free transferrin added to the media is indicated in parentheses. For comparison, all flow cytometry experiments included a unstained cells (cells) and nonfunctional fluorescently labeled aptamer control (cntrl).

FIG. 2(A)-2(D). Selection of aptamer which bind the human transferrin receptor. (A) Progress of the selection. The aptamer library from indicated rounds was hybridized to an AF488 labeled reverse primer and assayed by flow cytometry for binding to Jurkat cells. "oligo only" indicates cells treated with only the AF488 labeled reverse primer. (B) Sequence of clones isolated from round 5 of the selection. Clones capable of binding Jurkats cells are indicated with a (+) while those which showed no staining are indicated with a (−). Sequences are shown without the 5' and 3' constant regions. (SEQ ID NOS: 29-38, top to bottom, respectively, with sequences C2, C4/C8 and C11 being SEQ ID NOS: 29, 30 and 31, respectively). (C) Analysis of selected clones by flow cytometry on Jurkat cells. Aptamer labeling was performed as in (A). The identity of the clones are as indicated. (D) Bright field and fluorescent microscopy images of HeLa cells following incubation with RNA from Round 0 or the full length clone 2 (100 nM). RNAs were labeled by hybridization to AF546-labeled reverse primer. For comparison cells were also imaged following treatment with biotinylated transferrin complexed to AF546-labeled streptavidin (100 nM). Scale bars, 10 µm.

FIG. 3(A)-3(D). Comparison of anti-TfR binding clones c2, c4 and c11. (A) Sequences of clones c2, c4 and c11 with constant regions (underlined) (SEQ ID NOS: 39-41, top to bottom, respectively). The additional 3' constant region used for hybridization of a fluorescent probe for flow cytometry is not shown. Invariant residues shared between the clones are colored red. (B) Functional clones share a common fold. mfold predicted structure of c2, c4 and c11. Conserved residues highlighted in red (A) have been circled. The 5' and 3' ends of the sequences have been removed for clarity. (C) Minimization of c2. Truncations were made by runoff transcription from the corresponding dsDNA templates. All sequences share an additional 3' constant region used for hybridization to a fluorescent probe for flow cytometry (not shown). The conserved regions are highlighted in red. Residues added to start transcription, force pairing or introduce a tetraloop are indicated in green. The stem loop taken from c11 is indicated in blue. (SEQ ID NOS: 28 and 42-50, top to bottom, respectively, with c2.min being SEQ ID NO:50). (D) mfold predicted structure of minimized anti-TfR aptamer c2.min (SEQ ID NO:50).

FIG. 4(A)-(D). Binding analysis of anti-TfR clone c2. (A) Binding constant for the full length aptamer c2 (red) or the minimized variant c2.min (blue) were determined by dual filter binding assay using 32P-labeled RNA. The binding constants are as indicated. (B) Representative data for the determination of the apparent binding constant for the AF488-c2.min on Jurkat cells using flow cytometry. (C) Plot of the mean fluorescence from data collected in (B) versus the aptamer concentration used to determine the apparent binding constant for c2.min on Jurkat cells. The binding constant is as indicated. (D) c2.min binds multiple different cancer cell lines. Flow cytometry experiments were performed at a final concentration of 100 nM aptamer using either an AF488-c2.min (red) or a non-binding control aptamer, AF488-cntrl.36. Unstained cells are shown in grey. The cell lines used for each experiment are as indicated. Each panel represents two or more experiments.

FIG. 5(A)-5(C). (A) Endocytosis is required for efficient cell staining by c2.min. Untreated Jurkat cells (red) or those arrested by treatment with a mixture of sodium azide and deoxyglucose (blue) were treated with an AF488-c2.min, for 1 hr in media at 100 nM. Cells were subsequently washed and analyzed by flow cytometry. Unstained cells are shown in grey. (B) Binding and uptake of AF488-c2.min by Jurkat cells in the presence of increasing concentrations of free transferrin. 100 nM aptamer was incubated with cells for 1 hr in media. The concentration of free transferrin added to the media is indicated in parentheses. Cells were washed and analyzed by flow cytometry. (C) Determination of the $IC_{50}$ for binding and uptake of AF488-c2.min and DY488-Tf. Experimental conditions were as in (B) and described in the Methods and Materials. $IC_{50}$ values are as indicated. Data represent the average of two independent trials.

Figures 6A, 6B, 6C:
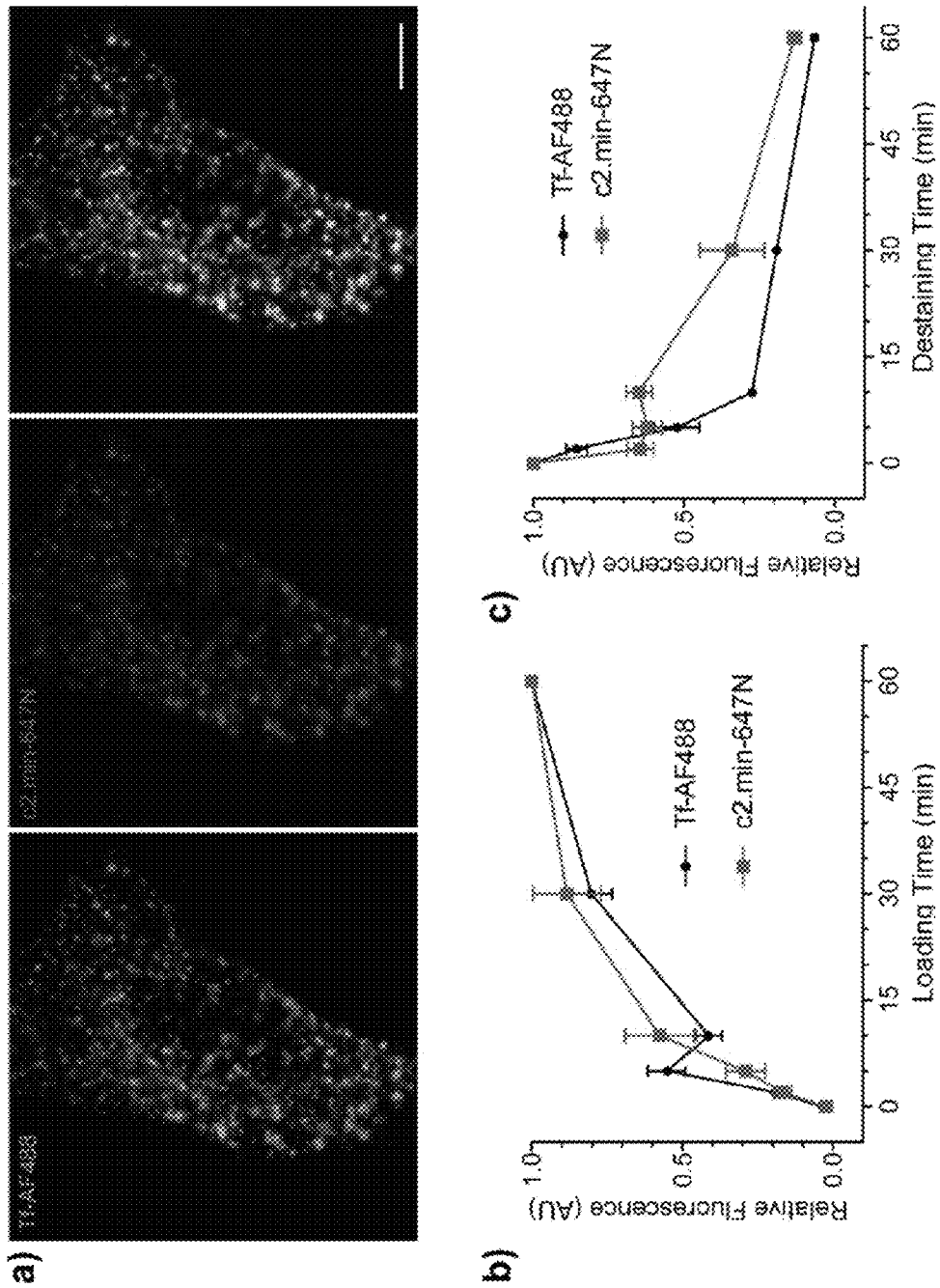

FIG. 6(A)-6(C). Labeled c2.min and Tf were followed by fluorescent microscopy. Confocal images of HeLa cells treated for 30 minutes with Tf-AF488 (50 µg/ml) and c2.min-647N (250 nM) show great subcellular co-localization (A). Time courses of the uptake of Tf-AF488 or c2.min-647N were monitored over 60 minutes (B). HeLa cells were loaded for 5 minutes with labeled c2.min or Tf, washed and transferred to fresh media for different time points. The loss of fluorescence was followed for 60 min (C). Data represent the average of three independent experiments with 15 to 20 images per time-point each. Error bars represent the SEM from three independent experiments. Scale bars, 5 µm FIG. 7(A)-7(I). (A) Uptake of SNALPs loaded with Cy5-labeled anti-EGFP siRNA and (B) knockdown of EGFP in HeLa-EGFP cells as determined by flow cytometry. Cells only (cells), targeted (c2.min) or non-targeted SNALPs (BME and cntrl.36) are as indicated. Transfection of the same Cy5-labeled anti-EGFP siRNA using HiPerfect was included for comparison (Transfection). Cells were treated as indicated for 24 hr, after which the media was changed. Cells were analyzed 48 hr after initial exposure to SNALPs. (C) Uptake of Cy5-labeled siRNA and (D) knockdown of EGFP in HeLa-EGFP cells in the absence or presence of 25 µM diferric human transferrin as determined by flow cytometry. Similar experiments using non-targeted SNALPs (BME and cntrl.36) were also performed. Data are representative of a minimum of three independent experiments. (E, F) qPCR analysis monitoring mRNA levels in HeLa-EGFP cells treated with SNALPS containing an anti-EGFP siRNA (e) or anti-lamin A/C siRNA (F) in the absence or presence (+Tf) of 25 uM transferrin. Cells only (cells), targeted (c2.min) or non-targeted liposomes (BME and cntrl.36) are as indicated. Cells were treated as indicated for 24 hr, after which the media was changed. Cells were analyzed 48 hr after initial exposure to SNALPs. All data represent the average of two or more independent trials using independent preparations of liposomes. (G, H) Concentration dependence of c2.min targeted uptake and gene knockdown in HeLa-EGFP cells. Experiments were conducted as described in (A). Concentrations are as indicated. Untreated cells (cells) are shown in grey. Similar experiments using non-targeted SNALPs (BME and cntrl.36) were performed. (I) Plot of liposome concentration versus mean fluorescence of Cy5 uptake (black) and EGFP knockdown (red).

Figure 8:
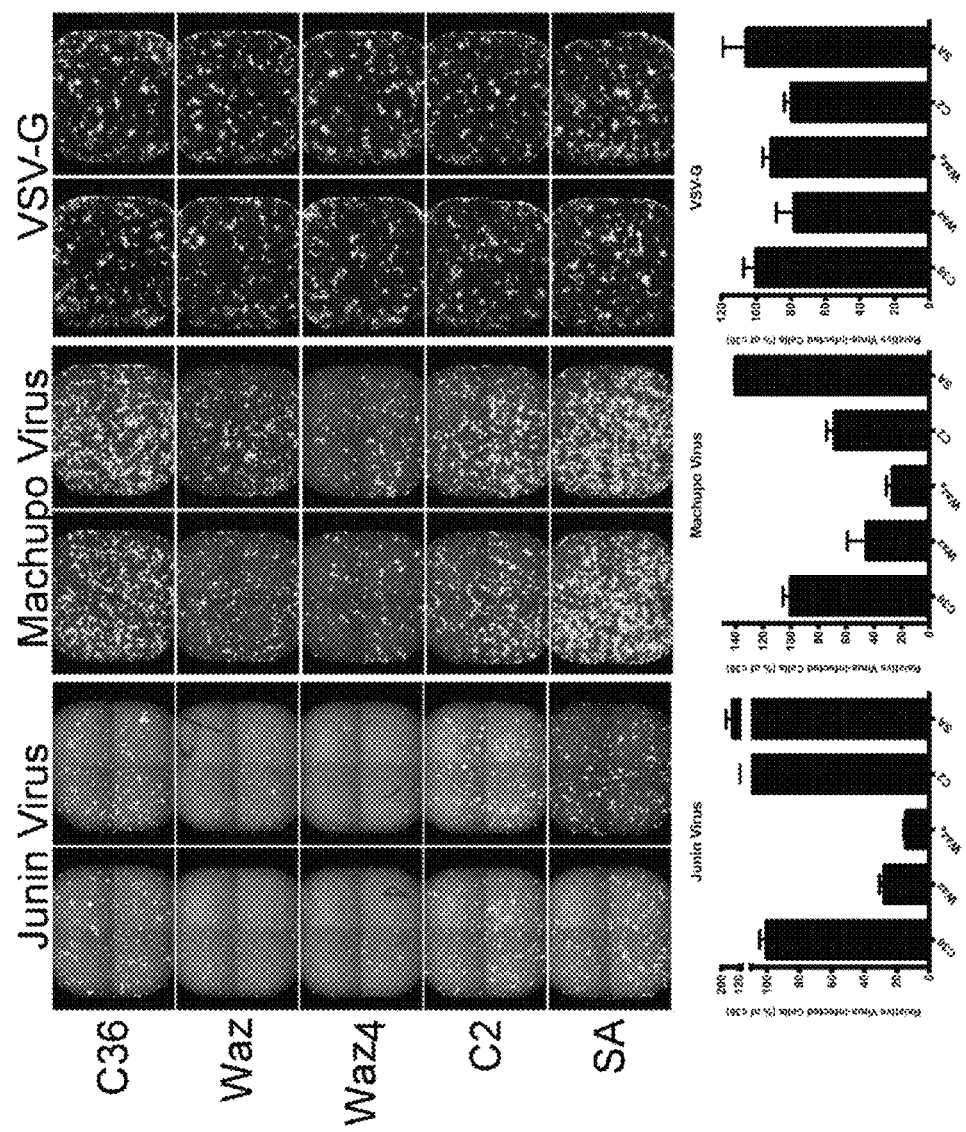

FIG. 8. U2OS cells imaged for expression of GFP, an indicator of viral infection. The total number of infected cells were determined by microscopic analysis. Under these conditions treatment with Waz (SEQ ID NO:51), or $Waz_4$ resulted in significant inhibition of viral infection with both VSV-Junin and VSV-Machupo with a greater inhibitory effect observed for $Waz_4 showed inhibition of VSV-Machupo but not VSV-Junin, while the controls, C36 and SA had no affect on infection. Similarly when experiments were performed with VSV-G, which bears the native VSV surface glycoprotein, no inhibition was observed.

DETAILED DESCRIPTION OF THE INVENTION

An isolated ribonucleic acid aptamer is provided comprising SEQ ID NO:1, 2, 3, 5, 10, 51 or 52-60. In an embodiment of the aptamer, one or more pyrimidine residues thereof comprise a 2' F group. In an embodiment, one or more purine residues thereof comprise a 2' F group. In an embodiment, one or more purine residues thereof comprise a 2' OMe group. In an embodiment, all the pyrimidine residues thereof comprise a 2' F group. In an embodiment, all the purine residues thereof comprise a 2' H group or a 2' OMe group. In an embodiment, the aptamer comprises SEQ ID NO:10.

In an embodiment, the aptamer binds a human transferrin receptor. In an embodiment, the aptamer does not compete for binding with human transferrin to a human transferrin receptor. In an embodiment, the aptamer binds a human transferrin receptor at a different site from which transferrin binds the human transferrin receptor. In an embodiment, the aptamer is conjugated to a liposome of 300 nm or less in diameter.

Also provided is an isolated ribonucleic acid aptamer of 60 bases or less which binds a human transferrin receptor but does not compete with human transferrin for binding to the human transferrin receptor.

Also provided is a composition comprising any of the aptamers described herein. In an embodiment, the composition comprises a pharmaceutically acceptable carrier.

Also provided is a composition, comprising any of the aptamers described herein conjugated to one of an oligonucleotide, a small organic molecule of less than 2000 daltons, a liposome or a nanoparticle.

Also provided is a composition, comprising a ribonucleic acid aptamer directed to a receptor, which aptamer is attached to a nanoparticle or liposome. In a preferred embodiment the composition comprises the aptamer attached to the liposome. In an embodiment, the liposome is 300 nm or less in diameter. In an embodiment, the aptamer is attached to the liposome by a thioether. In an embodiment, the liposome contains a nucleic acid or a small organic molecule of less than 2000 daltons. In an embodiment, the liposome contains a nucleic acid and the nucleic acid is an shRNA or an siRNA. In an embodiment, the liposome contains a small organic molecule of less than 2000 daltons and the small organic molecule is an anti-cancer therapeutic or is a drug which acts in the central nervous system of a mammal. In an embodiment, the liposome comprises one or more of 1,2-Distearoyl-sn-glycero-3-phosphocoline (DSPC), cholesterol and 1,2-distearoyl-sn-glycero-3-phosphoethanolamine (DSPE). In an embodiment, the receptor is a transferrin receptor. In an embodiment, the transferrin receptor is a human transferrin receptor. In an embodiment, the aptamer comprises SEQ ID NO:1, 2, 3, 5, 10, 29, 30, 31, 50, 51 or 52-60.

Also provided is a method of delivering a molecular entity to a receptor-expressing cell in a subject comprising administering to the subject any of the compositions described herein, wherein the molecular entity is conjugated to the aptamer or contained in a liposome attached to the aptamer, so as to thereby deliver the molecular entity to a transferrin receptor-expressing cell. In an embodiment, the receptor-expressing cell is a cancer cell. In an embodiment, the receptor-expressing cell is a brain capillary endothelial cell. In an embodiment, the aptamer composition is administered peripherally and the method effects delivery of the molecular entity to the central nervous system of the subject. In an embodiment, the molecular entity is a small organic molecule of less than 2000 daltons. The small organic molecule of the invention is, in an embodiment, an anti-cancer therapeutic. In an embodiment, the liposome attached to the aptamer encapsulates an anti-cancer therapeutic. In an embodiment, the liposome attached to the aptamer encapsulates an antibiotic, a vaccine, an analgesic, or a hormone. In an embodiment, the liposome attached to the aptamer encapsulates a amphotericin B, cytarabine, daunorubicin, doxorubicin, cisplatin, IRIV vaccine, morphine, or verteporfin. In an embodiment, the anti-cancer therapeutic is a cytotoxic agent. In an embodiment, the cytotoxic agent is a maytansinoid, an alkylating agent, an anti-metabolite, a plant alkaloid or terpenoid, or a cytotoxic antibiotic. In embodiments, the cytotoxic agent is cyclophosphamide, bleomycin, etoposide, platinum agent (cisplatin), fluorouracil, vincristine, methotrexate, taxol, epirubicin, leucovorin (folinic acid), or irinotecan.

In an embodiment, the liposome attached to the aptamer encapsulates a molecular entity which is small molecule that is active in a mammalian central nervous system (CNS). Non-limiting examples of such small molecules (2000 daltons or less) include an analgesic, an antitussive, a drug used medically in treatment of motor disorders, a drug used medically in treatment of hypertension, an anxiolytic, a sedative, antiepileptic, an antidepressant, a mood stabilizing drug, an antipsychotic, an Alzheimer's medication or a Parkinson's medication.

In an embodiment of the method, the receptor is a transferrin receptor. In an embodiment, the transferrin receptor is a human transferrin receptor.

In an embodiment of the method, the aptamer comprises SEQ ID NO:1, 2, 3, 5, 10, 29, 30, 31, 50, 51 or 52-60. In an embodiment of the method, the aptamer is less than 60, 50, 40 or 30 nucleotides in length.

In an embodiment, the molecular entity is a nucleic acid. In an embodiment, the molecular entity is an siRNA or an shRNA. In an embodiment, the siRNA is double-stranded, with each strand 19-21 nucleotides in length. In an embodiment, the siRNA or shRNA targets a mammalian oncogene. In an embodiment, the siRNA or shRNA targets a mammalian gene the expression of which that is up-regulated in a cancer. In an embodiment, the siRNA or shRNA is directed against a transcript encoding lamin or EGFR.

Aptamers, unless otherwise specified, are RNA or DNA molecules, or comprise both ribonucleotide residues and deoxyribonucleotide residues, and are generally generated from large combinatorial libraries ($10^{14}$-$10^{15}$) of nucleic acids. This may be done by a process of in vitro selection or by SELEX (Systematic Evolution of Ligands by Exponential Enrichment) which targets a specific protein or molecular target. They are generated though a process that relies on binding. Aptamers are thus nucleic acids (oligonucleotides, often oligoribonucleotides—a ribonucleic acid aptamer) which bind a specific protein or molecular target, typically with nanomolar or subnanomolar affinity. Generally, aptamers discriminate against molecules closely related to the target molecule.

The aptamers of the invention may comprise nucleosides. A "nucleoside" as used herein is a glycosylamine consisting of a base bound to a ribose or deoxyribose sugar via a beta-glycosidic linkage. Examples include cytidine, uridine, adenosine, guanosine, thymidine and inosine. Nucleosides can be phosphorylated by specific kinases in the cell on the sugar's primary alcohol group (—$CH_2$—OH), producing nucleotides, which are the molecular building blocks of DNA and RNA. Nucleosides can be produced by de novo synthesis pathways, particularly in the liver, but they are more abundantly supplied via ingestion and digestion of nucleic acids in the diet, whereby nucleotidases break down nucleotides (such as the thymine nucleotide) into nucleosides (such as thymidine) and phosphate.

The aptamers of the invention may comprise nucleoside analogs. A "nucleoside analog" is a nucleoside structurally similar to the naturally occurring residues in RNA and DNA, used in medicine and in molecular biology, and which can be incorporated, e.g. chemically, into an oligonucleotide or nucleic acid by formation of a phosphodiester bond or equivalent with one or two residues of the residue chain depending on whether the nucleoside analog is in a terminal or intra-chain position, respectively. Nucleic acids are chains of nucleotides, which are composed of three parts: a phosphate backbone, a pucker-shaped pentose sugar, either ribose or deoxyribose, and one of five nucleobases. A nucleoside analogue differs from a nucleoside by having any one or more of its hydroxyl, base or sugar groups altered, as long as the alteration does not prevent the nucleoside analogue from being incorporated into an oligonucleotide such as an aptamer, internalizing nucleic acid or tumor-homing nucleic acid. In an embodiment of the invention the nucleoside analogue(s) are one or more of the following: a deoxyadenosine analog, a deoxycytidine analog, a deoxyguanosine analog, a (deoxy-)thymidine analog, and/or a deoxyuridine analog. Typically the analogue nucleobases confer, among other things, different base pairing and base stacking proprieties. The ribonucleic acid aptamers of the invention may thus comprise nucleoside analogs.

Nucleoside analogs as envisaged in the current invention include, but are not limited to, cytosine arabinoside, fludarabine, cladribine, acyclovir, 2',3'-dideoxyinosine; 9-β-D-ribofuranosyladenine; 1β-arabinofuranosylcytosine; arabinosylcytosine; 4-amino-5-fluoro-1-[(2R,5S)-2-(hydroxymethyl)-1,3-oxathiolan-5-yl]-1,2-dihydropyrimidin-2-one; 2',3'-dideoxy-3'-thiacytidine; 2'-3'-dideoxycytidine; {(1S,4R)-4-[2-amino-6-(cyclopropylamino)-9H-purin-9-yl]cyclopent-2-en-1-yl}methanol; 2-Amino-9-[(1S,3R,4S)-4-hydroxy-3-(hydroxymethyl)-2-methylidenecyclopentyl]-6,9-dihydro-3H-purin-6-one; 2'-3'-didehydro-2'-3'-dideoxythymidine; 1-(2-deoxy-β-L-erythro-pentofuranosyl)-5-methylpyrimidine-2,4(1H,3H)-dione; 1-[(2R,4S,5S)-4-azido-5-(hydroxymethyl)oxolan-2-yl]-5-methylpyrimidine-2,4-dione; 1-[(2R,4S,5R)-4-hydroxy-5-(hydroxymethyl)oxolan-2-yl]-5-iodo-1,2,3,4-tetrahydropyrimidine-2,4-dione; 1-[4-hydroxy-5-(hydroxymethyl)oxolan-2-yl]-5-(trifluoromethyl) pyrimidine-2,4-dione; 5-Fluoro-2'-deoxycytidine; 5-Fluorodeoxycytidine; Floxuridine (5-Fluoro-1-[4-hydroxy-5-(hydroxymethyl)tetrahydrofuran-2-yl]-1H-pyrimidine-2,4-dione); 4-amino-1-(2-deoxy-2,2-difluoro-β-D-erythro-pentofuranosyl)pyrimidin-2(1H)-one; 2',2'-difluoro-2'-deoxycytidine; (8R)-3-(2-deoxy-β-D-erythro-pentofuranosyl)-3,4,7,8-tetrahydroimidazo[4,5-d][1,3]diazepin-8-ol.

The ribonucleic acid aptamers of the invention may comprise, on their constituent nucleotides, 2' modifications. Preferred modifications are 2' F on pyrimidines and 2' H or 2' OMe on purines.

In an embodiment, of the methods, compositions and aptamers described herein, the aptamer comprises SEQ ID NO:1, 2, 3, 5, 10, 29, 30, 31, 50, 51 or 52-60 with 0, 1, 2, 3, 4, 5, 6, 7, 8, 9, or 10 additional nucleotide residues at the 3' end thereof, and, independently, 0, 1, 2, 3, 4, 5, 6, 7, 8, 9, or 10 additional nucleotide residues at the 5' end thereof.

The present invention provides aptamers that are ribonucleic acid or deoxyribonucleic acid or mixed ribonucleic acid and deoxyribonucleic acid or which are analogs thereof, especially via modification of 2' groups on purines and/or pyrimidines. Aptamers of the invention may be single stranded. In some embodiments, the aptamers of the invention comprises at least one chemical modification (other than the included nucleoside analog(s), if included). In some embodiments, the chemical modification is selected from the group consisting of: a chemical substitution at a sugar position; a chemical substitution at a phosphate position; and a chemical substitution at a base position, of the nucleic acid. In other embodiments, the chemical modification is selected from the group consisting of: incorporation of a modified nucleotide, 3' capping, conjugation to a high molecular weight, non-immunogenic compound, conjugation to a lipophilic compound, and incorporation of phosphorothioate into the phosphate back bone. In a preferred embodiment, the non-immunogenic, high molecular weight compound is polyalkylene glycol, more preferably polyethylene glycol. In an embodiment the chemical modification is an inverted thymidine cap. In an embodiment the chemical modification is once or more phosphorothioate backbone modification(s). In a preferred embodiment, the aptamer is modified at a 2' group of one or more purines thereof and/or at a 2' of one or more pyrimidines thereof.

Aptamers of the present invention can be administered by any appropriate route or means, including topically, parentally or enterally. In non-limiting examples, administration is by subcutaneous injection (aptamer bioavailability via subcutaneous administration is >80% in monkey studies (Tucker et al., J. *Chromatography* B. 732: 203-212, (1999)), intravenously, intranasally (lower and/or upper epithelia), or by direct injection into the desired tissue or organ. With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers allows them to penetrate into areas of conformational constrictions that do not allow for antibodies or antibody fragments to penetrate, presenting yet another advantage of aptamer-based therapeutics or prophylaxis. In an embodiment of the methods disclosed herein, the method effects delivery of the molecular entity to the central nervous system of the subject.

The present invention additionally provides a pharmaceutical composition comprising a therapeutically effective amount of the aptamer or the aptamer composition and a pharmaceutically acceptable carrier. The pharmaceutical composition may comprise the aptamer comprising the oligonucleotide, nucleoside or nucleoside analog prepared for selective introduction in a subject's cells in a pharmaceutically acceptable carrier. Alternatively, the pharmaceutical composition may consist essentially of the aptamer comprising the oligonucleotide, nucleoside or nucleoside analog prepared for selective introduction in a subject's cells in a pharmaceutically acceptable carrier, i.e. having no other pharmaceutically active ingredients. Yet alternatively, the pharmaceutical composition may consist of the aptamer or aptamer conjugate or aptamer-liposome composition prepared for selective introduction in a subject's cells in a pharmaceutically acceptable carrier.

The pharmaceutically acceptable carrier must be compatible with the aptamer or aptamer conjugate or aptamer-liposome composition prepared for selective introduction in a subject's cells, and not significantly deleterious to the subject. Examples of acceptable pharmaceutical carriers include saline, carboxymethylcellulose, crystalline cellulose, glycerin, gum arabic, lactose, magnesium stearate, methylcellulose, powders, saline, sodium alginate, sucrose, starch, talc, and water, among others. Formulations of the pharmaceutical composition may conveniently be presented in unit dosage and may be prepared by any method known in the pharmaceutical art. For example, the aptamer, or aptamer conjugate or aptamer-liposome composition may be brought into association with a carrier or diluent, as a suspension or solution. Optionally, one or more accessory ingredients, such as buffers, flavoring agents, surface-active ingredients, and the like, may also be added. The choice of carriers will depend on the method of administration. The pharmaceutical composition can be formulated for administration by any method known in the art, including but not limited to, intravenously and orally. The pharmaceutical composition would be useful for administering the aptamer prepared for selective introduction of a cargo molecule (such as an anticancer drug) into a subject's cells to a subject to prevent or treat cancer or to prevent or treat viral infection, or to deliver the cargo to the CNS of a mammal. These amounts may be readily determined by one of a variety of standard pharmacological approaches. In one embodiment, there may be a number of active pharmaceutical ingredients in the formulation or composition aside from the aptamer. In this embodiment, the other active pharmaceutical ingredients in the formulation or composition must be compatible with the aptamer.

The aptamers of the invention can be chemically synthesized if desired, or transcribed from appropriate encoding nucleic acids and modified during or after sequence synthesis if desired. The aptamers of the present invention, with or without included one or more nucleoside analogs, can be stored in a variety of forms, including as lyophilized powders.

As used herein, a "liposome, is an artificially-prepared vesicle composed of a lipid bilayer. In an embodiment, the liposome is 300 nm or less in diameter. In a preferred embodiment, the liposome is 200 nm or less in diameter. In a preferred embodiment, the liposome is between 100 and 200 nm in diameter. In an embodiment, the liposome is 100 nm or less in diameter. In a preferred embodiment, the liposome comprises phospholipids. In an embodiment, the liposome is functionalized, for example with one or more PEG molecules on the external surface. In an embodiment, the liposome is a neutral liposome. In an embodiment, the liposome composition comprises a SNALP.

In an embodiment of the methods, the aptamer selectively introduces itself, and any molecular entity conjugated or otherwise attached thereto into a target. As used herein, "selective introduction," or grammatical equivalent thereof, means introduction of the entity being "selectively introduced" into the target in preference to other targets. For example, an oligonucleotide for selectively introduced into a tumor cell is accumulated into the tumor cell in preference to a non-tumor cell.

The cells may be any cells from any tissue in the subject including but not limited to, tumor cells, brain capillary endothelial cells, blood, skeletal, breast, cardiac, neural, renal, pancreatic, gastric, liver, splenic, muscle, or pulmonary tissue. The cells may be normal, diseased, cancerous or may be infected with a virus or other pathogen.

This invention provides a method of inhibiting a New World arenavirus from infecting a cell comprising contacting the cell with an amount of a ribonucleic acid aptamer, or an oliogimer thereof, which binds a transferrin receptor effective to inhibit a New World arenavirus from infecting a cell.

This invention also provides a method of treating a subject exposed to a New World arenavirus comprising administering to the subject an amount of a ribonucleic acid aptamer, or an oligomer thereof, which binds a transferrin receptor effective to inhibit a New World arenavirus from infecting a cell and treat a subject exposed to a New World arenavirus.

In an embodiment, the transferrin receptor is a human transferrin receptor. In an embodiment, the ribonucleic acid aptamer comprises SEQ ID NO:1, 2, 3, 5, 10, 29, 30, 31, 50, 51, or 52-60. In a preferred embodiment, the New World arenavirus is a New World hemorrhagic fever arenavirus. In a embodiment, the New World arenavirus is Junin virus or Machupo virus. In an embodiment, the ribonucleic acid aptamer comprises SEQ ID NO:1, 2, 3, 5, 10, 29, 30, 31, 50, 51, or 52-60. In a preferred embodiment, the ribonucleic acid aptamer comprises SEQ ID NO:51.

In an embodiment, one or more pyrimidine residues of the ribonucleic acid aptamer comprise a 2' F group, and/or wherein one or more purine residues thereof comprise a 2' F group, and/or wherein one or more purine residues thereof comprise a 2' OMe group, and/or wherein all the pyrimidine residues thereof comprise a 2' F group, and/or wherein all the purine residues thereof comprise a 2' H group or a 2' OMe group.

In an embodiment, the ribonucleic acid aptamer comprises GGGGGAUCAAUCCAAGGGACCCGGAAACG-CUCCCUUACACCCC (SEQ ID NO:50) or GGGUUCUACGAUAAACGGUUAAUGAUCAGC-UUAUGGCUGGCAGUUCCC (SEQ ID NO:51).

In an embodiment, the ribonucleic acid aptamer comprises GGGGGAUCAAUCCAAGGGACCCGGAAACG-CUCCCUUACACCCC-idT (SEQ ID NO:50) or GGGUUCUACGAUAAACGGUUAAUGAUCAGC-UUAUGGCUGGCAGUUCCC-idT (SEQ ID NO:51), wherein idT is an inverted dT residue.

In an embodiment, all G and A residues comprise a 2'OH group. In an embodiment, all C and U residues comprise a 2'F group.

In an embodiment, the oligomer is administered.

As used herein "and/or", for example as in option A and/or option B, means the following embodiments: (i) option A, (ii) option B, and (iii) the option A plus B, and any subset of such options, including only one option.

The subject may be any subject. Preferably, the subject is a mammal. More preferably, the subject is a human.

All combinations of the various elements described herein are within the scope of the invention unless otherwise indicated herein or otherwise clearly contradicted by context.

Where a numerical range is provided herein, it is understood that all numerical subsets of that range, and all the individual integers contained therein, are provided as part of the invention. Thus, for example, an oligonucleotide which is from 5 to 25 nucleotides in length includes the subset of oligonucleotides which are 18 to 22 nucleotides in length, the subset of oligonucleotides which are 20 to 25 nucleotides in length etc. as well as an oligonucleotide which is 5 nucleotides in length, an oligonucleotide which is 6 nucleotides in length, an oligonucleotide which is 7 nucleotides in length, etc. up to and including an oligonucleotide which is 25 nucleotides in length.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1

Introduction: The transferrin receptor, CD71, TfR is an attractive target for drug development due to its high expression on a number of cancer cell lines and the blood brain barrier. This type II transmembrane glycoprotein is responsible for cellular iron transport and is found at low levels on the surface of many normal cell types. However, the receptor is highly expressed on cells with increased proliferation rates. In particular, increased expression is observed across a wide range of cancer cells where increased expression is associated with poor prognosis. The receptor is also expressed at high levels on the blood brain barrier where it has been shown to be a route for ferrying cargoes across the blood brain barrier. Thus, ligands which target this receptor may prove highly valuable for altering the pharmacokinetics and dynamics of existing and future drugs. For example, recent work from Genentech has demonstrated that a bispecific antibody composed of an anti-TfR antibody and an anti-BACE1 antibody accumulated in the brains of mice leading to a greater reduction in brain amyloid-b (Ab) peptide production after a single systemic dose when compared to the anti-BACE1 antibody alone. Most recently, antibodies which bind this receptor have been shown to block infection by New World arenaviruses which cause human hemorrhagic fever and utilize this receptor for cell entry.

Results: Aptamers have previously been identified which bind the human transferrin receptor and are rapidly endocytosed by cells expressing this receptor (see PCT International Application Publication, WO/2011/142798, published Nov. 17, 2011, Levy et al., hereby incorporated by reference in its entirety). Three different aptamers were identified therein which share a core binding motif. While those aptamers are useful targeting agents, when the archetype aptamer, "C2", was assayed for binding the transferrin receptor in the presence of the natural ligand for the transferrin receptor, human transferrin (hTf), binding and cell uptake were significantly inhibited (FIG. 1A).

Free transferrin is present in the blood in three major forms which display differential binding affinities for the receptor: the low affinity apo-form (Kd=~4 μM) and the high affinity monoferric (Kd=~200 nM) and diferric forms (Kd=~10 nM). The total Tf concentration in serum is ~25 μM with the high affinity forms of the protein typically present at levels ranging from ~2 to 10 μM depending on the level of iron in the blood. As shown in FIG. 1A, as the concentration of diferric hTf was increased to 25 μM, C2 showed a decrease in observed binding and cellular uptake, although it should be noted that the aptamer still shows significant uptake under simulated physiological conditions (FIG. 1A; 2 uM, orange). Interestingly, a similar assay performed using fluorescently-labeled iron-loaded transferrin instead of the aptamer yielded a slightly lower $IC_{50}$ (~150 nM) demonstrating that this aptamer binds to the receptor slightly better than the natural ligand and is thus a superior molecule for targeting.

Herein additional experiments were performed to identify an anti-TfR aptamer which binds the transferrin receptor and which is not inhibited for binding by human transferrin. To achieve this goal, rounds of in vitro selection using the RNA population isolated from the 5th round of this laboratory's original selection against Jurkat cells, a human T lymphocyte cell line that expresses high levels of this receptor. To ensure the identification of aptamers which bind independent of Tf, each round was conducted in the presence of a superphysiological concentration (25 μM) of the high affinity diferric Tf. Analysis of the Round 10 population revealed aptamer variants with various levels of activity in the presence of diferric Tf, with the best aptamer variant, clone 1036, retaining full activity under these conditions (FIG. 1C). Importantly, this aptamer was subsequently partially minimized, rendering it amenable to chemical synthesis. The sequences of clone 1036, and the best performing minimized variants, are shown in Table I.

TABLE I

The sequences of clone 1036 and the best performing minimized variants. The function column shows the relative activity at the transferrin receptor. (SEQ ID NOS: 1-14, top to bottom, respectively).

| variant | function | sequence |
|---|---|---|
| 1036 | (++) | GGGAGGUGAAUGGUUCUACGAUAAACGGUUAAUGACCAGCUUAUGGCUGGCAGUUCCUAUAGCACCAACUACAUGCGAGAUGACCACGUAAUG |
| 36a | (++) | GGGUGAAUGGUUCUACGAUAAACGGUUAAUGACCAGCUUAUGGCUGGCAGUUCCUAUAGCACCC |
| 36b | + | GGGAGUUCUACGAUAAACGGUUAAUGACCAGCUUAUGGCUGGCAGUUCCUCCC |
| 36c | - | GGGAGUUCUAGUUAAUGACCAGCUUAUGGCUGGCAGUUCCUCCC |
| 36d | + | GGGUUAAUGACCAGCUUAUGGCUGGCAGUUCCC |
| 36e | - | GGGUGAAUGGUUCUACGAUAAACGGGUUAAUGACCAGCUUAUGGCUGGCAGUUCCCUAUAGCACCC |
| 36f | - | GGGUGAAUGGUUCUACGAUAAACGGUUAAUGACCGAAAGGCAGUUCCUAUAGCACCC |
| 36g | - | GGGUGAAUCAUAAACGGUUAAUGACCAGCUUAUGGCUGGCAGUUCCUACAGCACCC |
| 36h | - | GGGUGAAUGGUUCUACGAUAAACGGCUUAAUAGUUGCCUAUAGCACCC |
| 36i | (++) | GGGUUCUACGAUAAACGGUUAAUGACCAGCUUAUGGCUGGCAGUUCCC |
| Waz1 | - | GGGAACUACGAUAAACGGUUAAUGACCAGCUUAUGGCUGGCAGUUCCC |
| Waz2 | - | GGGUACGAUAAACGGUUAAUGACCAGCUUAUGGCUGGCACCC |
| Waz3 | - | GGGUACGAUAAACGGUUAAGGACCAGCUUAUGGCUGGCCCCC |
| Waz4 | - | GGGUACGACAAACGGUCAAUGACCAGCUUAUGGCUGGCACCC |

The identified active anti-human TfR aptamers are useful for delivering cargoes to TfR-expressing cells, and enhancing drug delivery across the BBB and to the CNS.

Example 2

Nuclease-stabilized aptamers which target the human transferrin receptor and are readily internalized by human cells. Aptamers were selected using a two-stage selection scheme which combines stringent selection against the recombinant protein followed by a 'functional' selection on cells grown in media [14]. Using this approach, a family of aptamers were identified which are readily and robustly internalized by a variety of human cancer lines known to express this receptor. A sequence analysis of functional clones revealed a conserved core motif from which were developed a minimized aptamer. To demonstrate their potential utility, minimized aptamers were used to functionalize siRNA-containing Stable Nucleic Acid Loaded Particles (SNALPs). Anti-TfR targeted SNALPs showed enhanced SNALP uptake and target gene knockdown in cells grown in culture when compared to non-modified SNALPs or those bearing a non-targeting aptamer control.

Selection of anti-TfR aptamers: In order to identify nuclease stabilized aptamers which target the human transferrin receptor and are readily endocytosed by cells, a hybrid in vitro selection protocol was used which combined stringent rounds of selection against recombinant protein with a function-based selection against cells. Selections were conducted using a 2'-fluoro-modified (2'F) RNA pool that contained a 50 nucleotide random sequence core flanked by primer binding sites. The 2'F modification can be readily incorporated during transcription by substituting 2'F CTP and 2'F UTP instead of the natural CTP and UTP and using the mutant T7 RNA polymerase protein Y639F [15, 16]. The resultant modified RNA is highly resistant to nuclease degradation and thus suitable for in vivo use [17].

An initial 4 rounds of selection were conducted using a His-tagged recombinant protein produced from Sf9 cells. For the initial round, ~3 copies of a library composed of ~1014 unique RNA sequences were utilized with ~2 µg recombinant hTfR immobilized on 20 µL Ni-NTA agarose. Following stringent washing, bound RNA was recovered by elution with imidazole and subsequently amplified. Following the first round, a negative selection step was employed in which the library was pre-incubated with Ni-NTA agarose prior to the positive selection step. For rounds 2, 3 and 4, the stringency of the selection was increased by dropping the concentration of the target protein 100-fold. However, when the Round 4 population was labeled using a fluorescently labeled oligonucleotide complementary to the 3' constant end of the library and analyzed the population's ability to stain Jurkat cells by flow cytometry, little or no improvement in binding was observed over the starting Round 0 library (FIG. 2(A)).

Figures 2A, 2B, 2C, 2D:
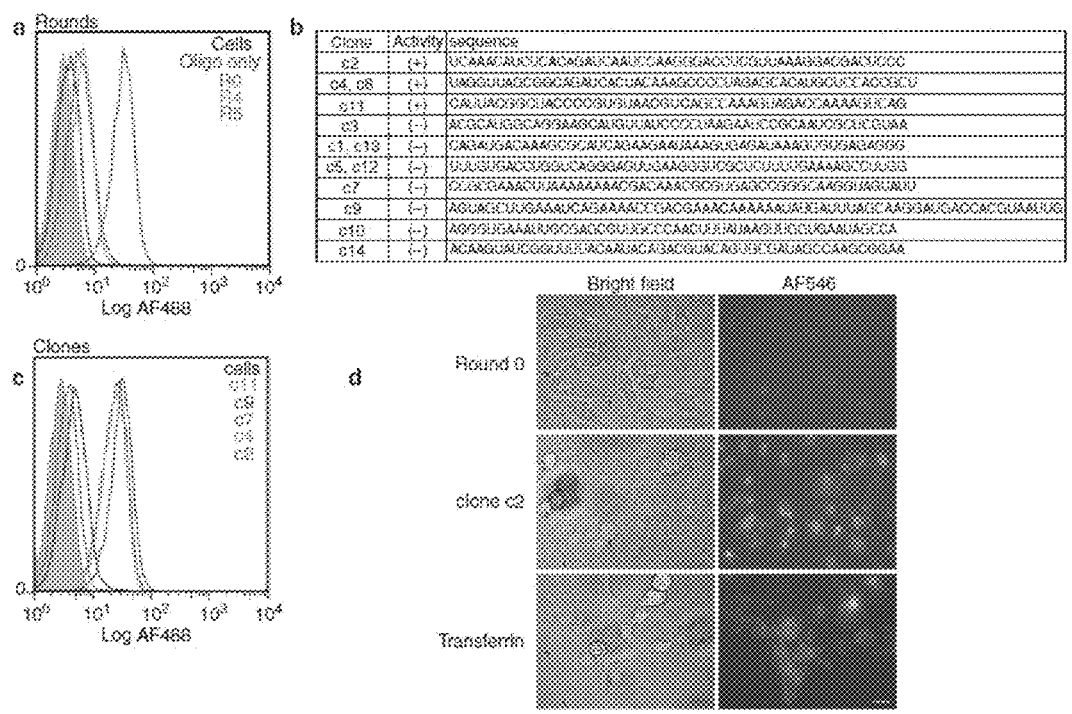

In order to ensure the identification of aptamers which could bind hTfR in the context of the cell surface and be readily endocytosed while potentially minimizing non-specific binding to the cell surface, following Round 4, an 'internalization selection' was performed on live HeLa cells, a human cervical cancer cell line known to express TfR [14]. In short, HeLa cells were incubated with the Round 4 aptamer library in media for one hour after which the cells were extensively washed and trypsinized. Following trypsinization, the recovered cells were treated with ribonuclease to remove any cell surface-bound RNA. Following an additional stringent wash, Trizol was used to extract total RNA from the cells, recovering any aptamers that have been internalized by the cells and thus protected from nuclease treatment. The recovered RNA was subsequently amplified, and the Round 5 population was assayed by flow cytometry on Jurkat cells. As shown in FIG. 2(A), the Round 5 population shows almost a 10-fold improvement in binding when compared to Round 4 or Round 0.

13 clones (FIG. 2(B)) were screened from the round 5 population by flow cytometry on Jurkat cells and 3 variants identified which bound robustly to Jurkat cells (FIG. 1c). Interestingly, while some sequences appeared multiple times in the population, only one of these (c4) turned out to be functional based on cytometric analysis. Importantly, when a fluorescently labeled aptamer (clone c2) was incubated with HeLa cells grown in culture for 1 hour, the fluorescence could be clearly seen as punctate foci in the cell cytoplasm (FIG. 2(D)), consistent with the biology of trafficking of the transferrin receptor.

Characterization and minimization of anti-TfR aptamers. A closer inspection of the sequences of individual functional clones identified from the selection revealed short regions of sequence similarity (FIG. 3(A); red and blue). Strikingly, the three aptamers could be folded into a set of similar structures in which the conserved regions occupied nearly identical positions along the stem loop comprising a large asymmetric bulge of 12 nucleotides containing a conserved nonamer (GAUCAYUMC; where Y=U or C and M=A or C) (SEQ ID NO:61) and trimer (AMA) as well as a second smaller, cytosine rich bulge situated 5 to 6 base pairs away (FIG. 2(B)). Using these structures as a guide, truncated versions of clone c2 were generated and tested to investigate the role of the conserved regions (FIG. 3(C)). As expected, deletion of the conserved 5'-nonamer (min.3) or modifications which converted the cytosine rich bulge to a loop (min.4) or removed it entirely (min.5) resulted in a total loss of activity as determined by flow cytometry. Interestingly, when the stem loop containing the cytosine rich bulge from c11 was replaced on the large asymmetric bulge from c2, the clone retained full activity further supporting the requirement both of these regions (min.9). More importantly, the analysis allowed identification of a minimal aptamer comprised of 42 nucleotides, c2.min, in which the terminal stem formed between the 3' and 5' ends was shortened and replaced the terminal loop with a stable GNRA tetraloop (FIG. 3(D)). The chemically synthesized aptamer bound recombinant protein with a Kd of 102 nM, ~5-fold worse than the full length clone c2 (Kd=17 nM; FIG. 4(A)).

A c2.min was generated and tested bearing a 3' inverted dT (deoxythymidine) residue for added stability and a 5' AlexaFluor 488 fluorescent tag to assess the molecule's ability to bind cells. When incubated with Jurkat cells in media for 1 hour, dramatic staining was observed by flow cytometry at concentrations as low as 10 nM (FIG. 4(B)). A plot of aptamer concentration versus mean fluorescence signal observed by cytometry yielded a $Kd_{apparent}$ on cells of 104 nM, a value similar to the binding constant observed with the recombinant protein observed in solution (FIG. 4(C)). Importantly, when similar control experiments were performed using a scrambled aptamer sequence, little or no background staining was observed (FIG. 4(C); cntrl.36).

Because the transferrin receptor is known to be overexpressed on numerous cancer cell lines, the ability of c2.min to bind different cell lines was assessed. c2.min bound to every cancer cell line tested including HeLa, 22Rv1, LnCAP, PC3, Ramos, A431, A549 and HT29 cells, as shown in FIG. 4(D). Experiments conducted with murine cell lines including mouse fibroblast 3T3 cells, mouse myoblast C2C12 cells and T lymphocyte EL4 cells failed to show any staining, demonstrating that the aptamer is specific for the human receptor (data not shown). Importantly, no significant binding was observed when the same cell lines were tested using a control aptamer, cntrl.36 (FIG. 4(D); blue).

Efficient staining requires endocytosis. Endocytosis of the transferrin receptor is an energy dependent process reliant on ATP [18]. The ability of c2.min to bind arrested cells was assessed. Interestingly, arrested cells (FIG. 5(A); blue trace) showed no staining, suggesting that the off rate for aptamer binding is quite rapid and it does not remain bound during the subsequent washing steps prior to cytometric analysis. Interestingly, no improvement in the staining of the arrested cells was observed when similar experiments were performed with the full length aptamer clone c2 (data not shown), which displayed a lower apparent binding constant against recombinant protein. This result suggests that the selection method may have yielded 'functional' aptamers more specifically tuned for internalization instead of aptamers that simply have a slow off-rate needed for high affinity binding.

C2 competes with transferrin for binding the receptor. The natural ligand for the transferrin receptor, transferrin (hTf), is present in blood at relatively high concentrations, ~25 µM with ~10-50% of this in the high affinity monoferric or diferric state [19, 20]. Therefore, it was assessed whether or not the selected aptamer would compete with this natural ligand for receptor binding and uptake. Using flow cytometry, the uptake of AF488-labeled c2.min was assessed on Jurkat cells in the presence of increasing concentrations of diferric hTf. As shown in FIG. 5(B), as the concentration of diferric hTf was increased to 25 µM, c2.min showed a decrease in binding with a plot of fraction aptamer bound versus the concentration of free transferrin yielding an IC50 of ~280 nM (FIG. 4(C)). Interestingly, a similar assay performed using fluorescently labeled iron loaded transferrin instead of the aptamer yielded a slightly lower $IC_{50}$ (~150 nM) demonstrating that the aptamer binds to the receptor slightly better than the natural ligand.

The uptake kinetics of hTf and of the c2.min aptamer were investigated. Cells were co-incubated with AF488-labeled hTf and atto647N-labeled c2.min. Following a 30 minute incubation, cells displayed the characteristic endosomal punctuated pattern obtained with labeled transferrin. Moreover, c2.min exhibits a vast co-localization with transferrin (FIG. 6(A)). When uptake was monitored over the course of a 60 minute period, the rates of uptake of the fluorescent cargoes showed no differences (FIG. 6(B)). Similar experiments in which cells were first loaded with either Tf-AF488 or c2.min-647N, washed and then placed in fresh media for different time points revealed that labeled c2.min washed-off more slowly than labeled Tf (FIG. 6(C)). This finding is consistent with the relative binding constants for iron free apo-transferrin (Kd=~4 µM) [21] and the aptamer (Kd=~100 nM).

Enhanced delivery of siRNA using anti-TfR aptamers. In order to assess the delivery ability molecular cargoes using anti-transferrin aptamers, siRNA encapsulated in liposomes were generated containing a Cy5 labeled anti-EGFP siRNA and gene knockdown investigated in HeLa cells engineered to constitutively express EGFP (HeLa-EGFP).

Using a scalable, extrusion free approach to making nucleic acid loaded liposomes [22], aptamer functionalized Stable Nucleic Acid-Lipid Particles, SNALPs, were generated utilizing a lipid formulation previously shown to be effective at delivering siRNA both in mice as well as non human primates [23], but replacing the surface PEG-2000 molecules with a thiol reactive PEG-2000-malemide. Following siRNA encapsulation and dialysis, the thiol-reactive liposomes were incubated with either a thiol-modified c2.min, a non-functional control aptamer (cntrl.36) or no aptamer at all (BME). Aptamer conjugations typically proceeded to ~90% within 4 hours as determined by gel electrophoresis. The liposomes were further characterized by dynamic light scattering and, consistent with previous reports, found to be ~180 nm in diameter with a polydispersity of ~20% [8, 22, 24]. Aptamer conjugation resulted in a slight increase in liposome size (Table II). Based on their size, the total mass of lipid used and the concentration of aptamer used in the conjugation, it was estimated that each liposome displayed ~60 aptamers per particle.

TABLE II

| Liposome size | | |
|---|---|---|
| surface modification | Diameter (nM) | Polydispersity (%) |
| none | 167 | 17 |
| cntrl.36 | 177 | 18 |
| c2 | 190 | 20 |

Figures 7A, 7B, 7C, 7D, 7E, 7F, 7G, 7H, 7I:
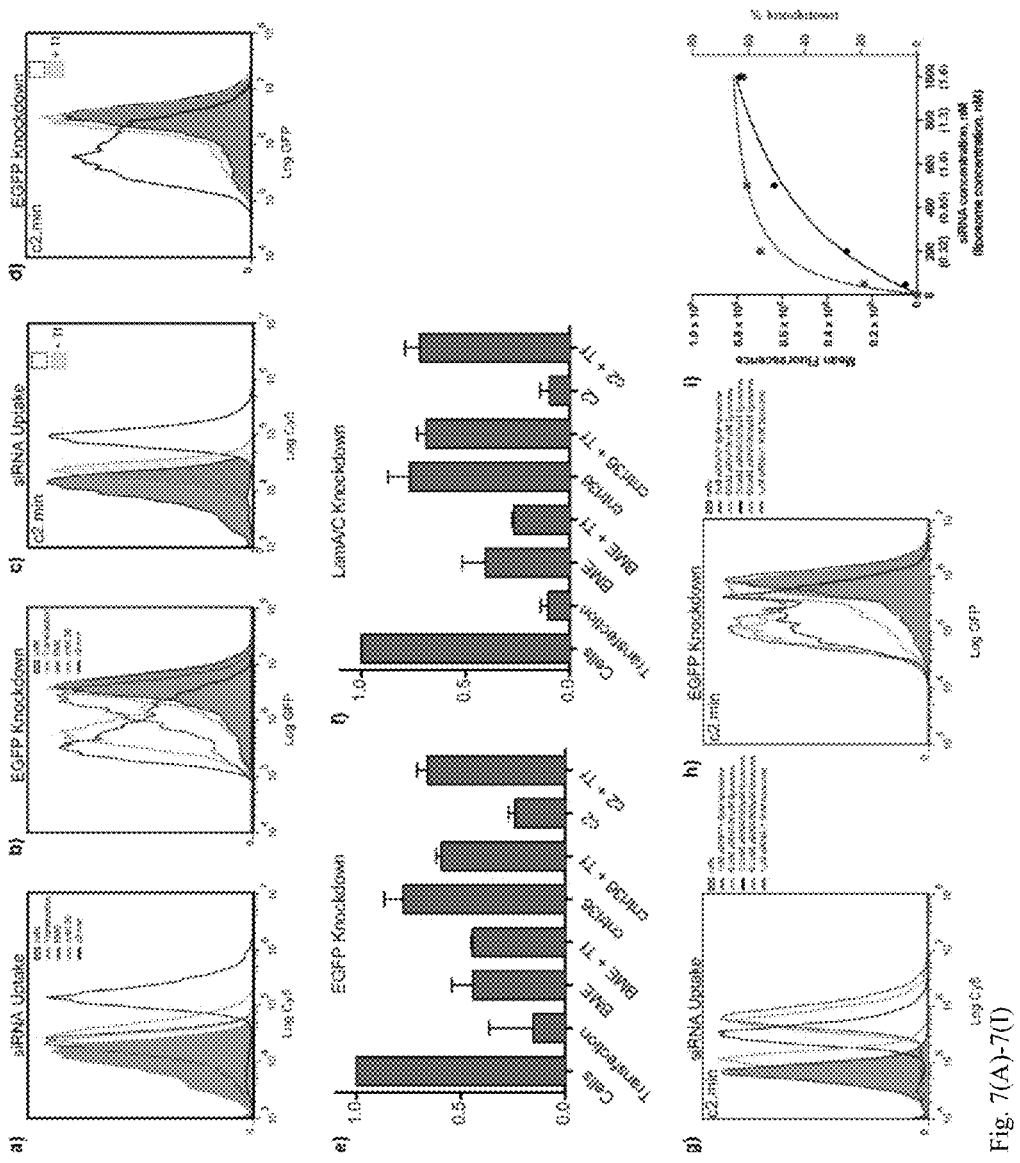

Liposome uptake (Cy5) and gene knockdown (EGFP) were assessed by flow cytometry using HeLa-EGFP cells 48 hours after treatment with aptamer targeted or control SNALPs containing a Cy5-labeled anti-EGFP siRNA. As shown in FIG. 7(A), the c2.min targeted SNALPs showed increased levels of uptake by cells when compared to both non-targeted SNALPs (BME) and those bearing the non-functional aptamer control (cntrl.36). More importantly, the enhanced uptake by the c2.min conjugated SNALPs also translated to an increased level of gene knockdown, as assessed by monitoring the decrease in the expression levels of the target protein EGFP (FIG. 7(B)).

To confirm that uptake by c2.min targeted SNALPs was mediated by binding and endocytosis via the transferrin receptor, similar experiments were performed using HeLa-EGFP cells and SNALPs loaded with a Cy5-labeled anti-EGFP siRNA but in the presence of free transferrin. Consistent with the competition studies performed with the free aptamer (FIG. 5(B),(C)), c2.min targeted SNALPs displayed reduced uptake when 25 µM transferrin was added to the cell culture media (FIG. 7(C)). When the same cells were analyzed for EGFP knockdown, c2.min targeted SNALPs showed a significant decrease in the level of knockdown of EGFP (FIG. 7(D)). The added transferrin had no effect on uptake or gene knockdown when treated with non-targeted (BME) or non-functional aptamer controls. Gene knockdown and the mechanism of uptake were further confirmed by using real time PCR to assess the level of EGFP mRNA degradation (FIG. 7(E)). Clone 1036 and the active variants thereof would be expected to perform at least as well, and likely better than the c2.min in the targeted SNALPs.

To ensure specificity, experiments were performed similar using an alternate siRNA which targets the housekeeping gene lamin A/C. HeLa-EGFP cells treated with SNALPs containing a Cy5-labeled anti-lamin A/C siRNA showed similar levels of siRNA uptake but failed to show a decrease in EGFP signal (data not shown). In contrast, real time PCR analysis of the treated cells revealed enhanced knockdown of lamin A/C mRNA when treated with c2.min targeted SNALPS as compared with non-targeted SNALPs or those bearing the non-functional aptamer control (FIG. 7(F)). Importantly, when these experiments were performed in the presence of 25 µM transferrin, only the samples treated with c2.min targeted SNALPs were affected, returning to near background levels of mRNA knockdown.

Nanoparticles and liposomes often benefit from the fact that targeting ligands are displayed in a polyvalent manner which can lead to significant enhancements in binding affinity through avidity effects [24, 25]. Indeed, at 200 nM siRNA, the concentration used in the delivery experiments, the concentration of liposomes is actually ~300 pM, which is far below the observed binding constant measured for the aptamer (100 nM). To explore this effect further, uptake (FIG. 7(G)) and knockdown experiments (FIG. 7(H)) were performed over a range of concentrations from 1 nM to 1 uM siRNA (1.6 pM to 1.6 nM liposome). Liposome binding/uptake displayed an apparent Kd of 530±160 pM (FIG. 6i), ~200-fold less than the aptamer alone. Gene knockdown displayed an EC50 of 85±30 pM (FIG. 6i) demonstrating that the siRNA pathway saturates long before the cell uptake pathway does. Consistent with the previous results, little background uptake and almost no change in EGFP expression is observed when similar experiments are performed with non-targeted SNALP controls.

Finally, the delivery of siRNA, especially via endosomal routes has the potential to lead to non-specific immune activation [25]. Therefore, the cellular immune response to cells treated with aptamer targeted SNALPS were assessed by monitoring the expression of OAS1, CDKL2 and interferon B by real time PCR. No increase in mRNA levels of these genes was observed indicating that aptamer mediated SNALP delivery did not induce any adverse cellular effects.

Discussion

While both DNA and RNA aptamers to the murine transferrin receptor have previously been reported, neither of these can be easily adapted for therapeutic or diagnostic purposes in humans, as they were selected against the mouse variant and do not cross react [13]. Additionally, because these aptamers are non-modified RNA and DNA, they are not serum stable and will require additional modifications and optimizations before use in vivo. In experiments conducted in this lab, a FITC-labeled version of the anti-murine transferrin receptor DNA aptamer did not stain murine fibroblasts (3T3) or T cells (EL4) in media (data not shown).

The nuclease-stabilized aptamers disclosed herein which bind the human transferrin receptor and are readily internalized by cells provide a means to specifically deliver cargoes to human cells which express this receptor.

Because the natural ligand for the transferrin receptor, transferrin, is present in blood at the relatively high concentration of ~25 µM, it was assessed whether the selected aptamers would compete with this ligand for binding. In serum, transferrin exists in three major forms: the low affinity apo-form (Kd=~4 µM) and the high affinity mono-ferric (Kd=~200 nM) and diferric forms (Kd=~10 nM) [21]. These high affinity forms of the protein are typically present at levels ranging from ~2 to 10 µM depending on the level of iron in the blood [19, 20]. In titration experiments in which the high affinity diferric transferrin was used as a competitor, significant aptamer binding and uptake were observed even at superphysiological concentrations of free ligand. When compared to fluorescently labeled transferrin, the c2-based aptamer displayed a more favorable $IC_{50}$ (~2-fold) than the natural ligand suggesting that these molecules would serve as superior in vivo targeting agents.

Based on the designs reported by Dassie et al (A10-SWAP; [37]) aptamer-siRNA chimeras were generated targeting the gene plk1 using the minimized aptamer c2.min as the targeting molecule. The aptamer-siRNA chimeras were readily taken up by HeLa, LNCaP and 22Rv1 cells at essentially the same levels as the free aptamer. However, the efficacy of the delivered siRNA proved very poor with no effect on cell viability observed (data not shown). Control experiments using the constructs reported by Dassie et al. which target the prostate specific membrane antigen (PSMA) on LnCAP and 22Rv1 cells (two cell lines known to express PSMA) also failed to elicit any effect on cell viability even when delivered at 100 times the published minimal effective dose (400 nM). While delivery was good, the lack of efficacy of this approach prompted identification alternate methods for the delivery of siRNA.

Nanoparticle based delivery systems are gaining much interest both in the lab and in the clinic, and aptamers have previously been shown capable of enhancing the delivery of nanoparticle and liposomal small molecule drug formulations [38-42]. With an interest in targeting siRNA, the c2.min aptamer was tested for its ability to enhance delivery of nanoparticle-based siRNA formulations. A lipid nanoparticle formulation called SNALPs (stable nucleic acid-lipid particles), which have previously been used to deliver siRNA to liver cells as well as solid tumors [43] and are currently undergoing clinical trials [44, 45], was investigated. While these neutral liposomes have previously been shown to associate with apo-E leading to efficient liver uptake, more recent work has demonstrated that the particles and their siRNA cargoes can be specifically targeted to other receptors by functionalizing the liposomal surface with ligands [46]. To this end, maleimide functionalized SNALPs were synthesized using an extrusion free approach [47]. This yielded liposomes approximately ~200 nm in diameter which was subsequently derivatized with a thiol-modified, minimized anti-TfR aptamer, c2.min. Liposomes of smaller size could be used in vivo. In this regard, the ease with which aptamers can be chemically synthesized and site specifically modified makes them ideal candidates for chemical conjugation and functionalization of nanoparticles.

Anti-TfR targeted SNALPs displayed both enhanced uptake and enhanced target gene knockdown when compared to SNALPs bearing a maleimide group which had been quenched with BME or those bearing a non-targeting control aptamer (FIG. 7(A)). Interestingly, SNALPs bearing the control aptamer performed worse than those quenched with BME suggesting that the negatively charged molecules on the surface of the liposome may inhibit interactions with serum ApoE and hinder uptake by this mechanism. To confirm the route of uptake of the anti-TfR targeted SNALPs, experiments were performed in the presence of 2 mg/mL human holotransferrin (diferric). Like with the free aptamer, at this concentration of free ligand, liposome binding was significantly decreased as was the observed gene knock down, confirming the link between receptor targeting and the observed enhanced function. Liposomes targeted using the 1036 clone and variants described herein would be expected to be even more efficacious than the c2.min based versions.

Materials and Methods

Cell lines and tissue culture. All cells were obtained from the American Tissue Culture Collection (ATTC; Manassas, Va.). HeLa, A431, and HT29 cells were cultured in DMEM (Invitrogen, Carlsbad, Calif.) supplemented with 10% FBS (Invitrogen). Jurkat, Ramos, 22Rv1 and LnCap cells were cultured in RPMI-1640 (Invitrogen) supplemented with 10% FBS. PC3 and A549 cells were cultured in F12K (Invitrogen) supplemented with 10% FBS. All cells were grown at 37° C. with 5% $CO_2$ and 99% humidity. Sf9 insect cells were grown at 27° C. in Grace's Insect Media (Invitrogen).

Protein production and purification. The plasmid pAcGP67A-TfR (Addgene) was used to express human transferrin receptor (hTfR) in insect cells (Sf9). The His-tagged protein was purified on Ni-NTA agarose, dialyzed to remove imidazole and concentrated to ~1 mg/mL for storage.

Selection of nuclease stabilized anti-TfR aptamers. The sequence of the N50 library used for selection was: 5'GGGAGGTGAATGGTTCTACGAT-N50-TTACATGC-GAGATGACCACGTAATTGAATTAAATGCCCGCCAT-GACCAG-3' (SEQ ID NO:15). The single stranded DNA library was synthesized such that N regions contained an equal probability of containing A, T, G, or C, as previously described [48]. Following deprotection, the library was gel purified by denaturing (7M urea) gel electrophoresis on an 8% polyacrylamide gel. The single stranded DNA library was amplified by PCR to generate double stranded DNA bearing a T7 promoter. The double-stranded pool was transcribed in vitro using the Y639F mutant of T7 RNA polymerase [15, 16] and 2'-fluoro (2'F) pyrimidines. The RNA was purified on a denaturing (7 M urea) 8% polyacrylamide gel.

For the initial round of selection ~3 copies were utilized of a library composed of ~1014 unique RNA sequences. Prior to each round, the library was thermally equilibrated in 30 uL HBSS (Hank's Buffered Saline Solution; Invitrogen) for 3 minutes at 70° C. and allowed to cool on the benchtop for at least 15 minutes. The sample was subsequently supplemented with 0.1% BSA, 1 μg/μL ssDNA and tRNA in a final volume of 50 μL of HBSS.

The thermally equilibrated aptamer library was incubated with 2 μg of recombinant hTfR immobilized on 20 μL of Ni-NTA agarose. Following a 30 minute incubation at room temperature, the resin was washed 5 times with 500 μL of HBSS, and then protein bound RNA was eluted by the addition of 400 μL HBSS containing 200 mM imidazole. Eluted RNA was recovered by ethanol precipitation, reverse transcribed, PCR amplified and re-transcribed into RNA for the subsequent round. Following the first round, a negative selection step was employed in which the library was pre-incubated with 200 μL of Ni-NTA agarose prior to the positive selection step. For rounds 2, 3 and 4, 5 μg of RNA was utilized, and the stringency of the selection was increased by dropping the number of target protein by 100-fold. This was achieved by resuspending 2 μg of protein immobilized on 20 μL of Ni-NTA agarose in 200 μL of HBSS and using 2 μL of the well mixed slurry. For these rounds, washing was facilitated by using a 0.45 micron spin filter to capture the trace amount of Ni-NTA resin. All incubations and washes (6×400 uL) were performed at 37° C.

For Round 5, an 'internalization selection' using HeLa cells was performed. To ensure that selected aptamers could easily be assayed by flow cytometry, the pool was combined with a 1.5 fold molar excess of reverse primer bearing a 5' fluorescent dye (AF488-CTGGTCATGGCGGGCATT-TAATTC) (SEQ ID NO:16). Following thermal equilibration in 50 μL of HBSS, the library was added to one well of a 24 well plate containing ~105 adherent HeLa cells in 300 μL DMEM supplemented with 10% FBS and 1 mg/mL tRNA and ssDNA (Sigma, St. Louis, Mo.) as blocking agents. Following a 1 hour incubation at 37° C., the cells were washed three times with 1 mL HBSS containing 0.1% sodium azide, once with 1 mL cold 200 mM glycine and 150 mM NaCl at pH 4, and three more times with HBSS. Cells were then lifted with 500 μL trypsin-EDTA containing 0.1% sodium azide, removed from the plate, washed with 1 mL HBSS and resuspended in 100 μL HBSS containing 5 μL Riboshredder RNAse cocktail (Epicentre, Madison, Wis.). Following a 5 minute incubation at room temperature, the cells were washed an additional three times with 1 mL of HBSS, and the total cellular RNA was recovered using Trizol extraction according to manufacturer's protocol (Invitrogen). The recovered RNA was reverse transcribed, amplified by PCR and transcribed back into RNA.

Minimized aptamers were generated by run-off transcription using the Y639F RNA polymerase and 2'-fluoro (2'F) pyrimidines. The RNA was purified on a denaturing (7 M urea) 8% polyacrylamide gel. The minimized 2'F RNA variants all bore the same 3' constant region (GAATTAAAT-GCCCGCCATGACCAG) (SEQ ID NO:17), which allow for hybridization of reverse primer bearing a 5' fluorescent dye. Binding assays were conducted using flow cytometry as described above.

Chemical synthesis of RNA aptamers. The minimized aptamer was synthesized in-lab on an Expedite 8909 DNA synthesizer (Applied Biosystems, Carlsbad, Calif.) using 2'-fluoro-deoxycytidine and 2'-fluoro-deoxyuridine phosphoramidites (Metkenin, Kuusisto, Finland). Unless noted otherwise, all reagents were purchased from Glen Research (Sterling, Va.). The aptamer was synthesized bearing a 5' thiol modification using a thiol-modifier C6 S-S phosphoramidite and a 3' inverted dT residue for added serum stability. The sequences of the minimized aptamer, c2.min, and a non-binding aptamer, cntrl.36, were: 5SGGGGGAU-CAAUCCAAGGGACCCGGAAACGCUCCCUUACAC-CCCt (SEQ ID NO:18) and 5SGGCGUAGUGAUUAUGAAUCGUGUGCUAAUA-CACGCCt (SEQ ID NO:19), respectively, where 't' is a 3' inverted dT and '5S' is the 5' thiol. All aptamers were synthesized with final dimethoxytrityl group on to facilitate purification. Following deprotection, aptamers were purified by reversed phase HLPC on a 10.∴50 mm Xbridge C18 column (Waters, Milford, Mass.) using a linear gradient of acetonitrile in 0.1M triethylammonium acetate at pH 7.0.

Thiolated aptamers were used to generate the Alexa-Fluor488 (AF488) or Atto-647 labeled aptamers used in cytometry or microscopy. Labeling was performed using AF488-C5-malemide (Invitrogen) or Atto-647-malemide (ATTO-TEC GmbH, Siegen, Germany) as follows: 10 nmoles thiolated aptamer was reduced using 10 mM tricarboxyethylphosphine in 100 μL of 0.1 M TEAA. Samples were heated at 70° C. for 3 minutes followed by incubation at room temperature for 1 hour. The reduced aptamers were desalted using Biospin 6 columns (BioRad, Hercules, Calif.) into PBS supplemented with 50 mM phosphate pH 7.5. To this, 10 μL of DMSO was added containing the fluorescent maleimide. Following an overnight reaction at 4° C., the aptamer was recovered by ethanol precipitation, resuspended in PBS and desalted an additional time using a Biospin 6 column. Dye to aptamer ratios were determined at 260 and 650 nm and were typically ~1. The absence of free dye in the final product was confirmed by reversed phase HLPC.

Aptamer binding by flow cytometry. Aptamer binding and uptake was assessed by flow cytometry. Rounds from each selection or isolated clones were first hybridized to the AF488-labeled reverse primer complementary to the 3' end of the library. Rounds or individual aptamers were incubated at 1 μM with 1.5 μM biotinylated oligonucleotide in DPBS heated to 70° C. for 3 minutes and then allowed to cool on the bench top for 15 minutes. Following hybridization, the aptamers were added to cells in the appropriate media supplemented with 1 μg/ml tRNA and sheared salmon sperm DNA (ssDNA) at final concentration of 100 nM.

For assays conducted on suspension cells, ~150,000 cells were incubated in a final reaction volume of 50 μL. For adherent cells, ~100,000 cells were incubated per well in a 24 well plate in 100 μL final volume. Unless otherwise noted, rounds/aptamers were incubated with cells for 1 hour at 37° C. Following incubation, adherent cells were trypsinized with 100 μL trypsin-EDTA for 5 minutes. The reaction was quenched by the addition of 1 mL FACS buffer, and the cells were pelleted and washed an additional time with FACS buffer before being resuspended in 500 μL FACS buffer containing 2 μg/mL 7-aminoactinomycin D stain (7AAD) to exclude dead cells in the analysis. Flow cytometry was performed on a FACScan or FACScalibur flow cytometer (Beckton Dickinson, Franklin Lakes, N.J.).

Fluorescence Microscopy. For microscopic analysis of Round 0 and full length c2 on HeLa cells, RNA was labeled by hybridization to an AF546 labeled oligonucleotide as described above for the flow cytometry experiments. As a control, 1 μM biotinylated transferrin (Invitrogen) was pre-incubated with 1 μM AF546-labeled streptavidin (Invitrogen). HeLa cells were grown as adherent monolayers in 8-chamber glass slide systems (Labtek, Nunc Nalgene International, Rochester, N.Y.). Thirty minutes prior to aptamer treatment, cells were blocked with 0.1 μg/mL tRNA and ssDNA in DMEM supplemented with 10% FBS at 37° C. Labeled Round 0, c2 or transferrin was added to the media to a final concentration of 100 nM, and the samples were incubated at 37° C. for 1 hour, after which the media was changed, and the cells were imaged on an Olympus IX71 inverted microscope.

Colocalization images (FIG. 6A)) of hTf-AF488 and c2.min-647N were obtained using a TCS (true confocal scanner) SP5 fluorescence microscope from Leica Microsystems GmbH, with a 1.4 N.A., 100× objective (Leica Microsystems GmbH). HeLa cells were exposed simultaneously to Tf-AF488 (50 μg/ml) and c2.min-647N (250 nM) for 30 minutes in Ringer buffer containing 10 μg/ml each of yeast tRNA and ssDNA as blocking agents. Coverslips were then taken out, washed thoroughly with Ringer buffer and placed in ice-cold paraformaldehyde (4%) for 30 minutes. Samples were quenched for 10 minutes with PBS containing 100 mM of glycine and NH4Cl. Finally cells were mounted in Mowiöl.

Uptake and washout experiments of transferrin or aptamer were imaged with an Olympus IX71 microscope equipped with 1.45 NA/100× objective. Images were captured with an Olympus F-View II CCD camera (all from Olympus, Hamburg, Germany). For uptake experiments, HeLa cells were washed in Ringer buffer (124 mM NaCl, 5 mM KCl, 2 mM $CaCl_2$, 1 mM $MgC_{12}$, 30 mM D-glucose and 25 mM HEPES, pH 7.4) and exposed to a mixture of Tf-AF488 (50 μg/ml) and c2.min-647N (250 nM) prepared in Ringer buffer containing 10 μg/ml each of yeast tRNA and ssDNA as blocking agents. After the specified times, coverslips were washed thoroughly, fixed in ice-cold paraformaldehyde (4%) for 30 minutes and then quenched for 10 minutes with PBS containing 100 mM of glycine and $NH_4Cl$. Finally cells were mounted in Mowiöl.

For monitoring the loss of fluorescence, HeLa cells were washed in Ringer buffer and exposed for 5 minutes to a mixture of Tf-AF488 (50 μg/ml) or c2.min-647N (250 nM) prepared in Ringer buffer containing 10 μg/ml each of yeast tRNA and sheared ssDNA as blocking agents. Cells were then briefly washed with a large volume (100 ml) of Ringer buffer and placed back into their complete medium inside the incubator (37° C. and 5% CO2). After the specified times, coverslips were taken out, washed with Ringer buffer and placed in ice-cold paraformaldehyde (4%) for 30 minutes. Samples were quenched for 10 minutes with PBS containing 100 mM of glycine and NH4Cl. Finally cells were mounted in Mowiöl.

Graphs represent the average data obtained from three independent experiments with 15 to 20 images per time-point each. Error bars represent SEM from three independent experiments.

Determination of binding constants. Binding constants were determined by nitrocellulose filter binding assays [49]. Aptamers were radiolabeled using T4 PNK (Optikinase, USBiologicals, Swampscott, Mass.) and gamma-32P-ATP (Perkin Elmer, Waltham, Mass.) following standard protocols. The full length c2 aptamer was generated by transcription as described above, and the terminal triphosphate was removed by treatment with alkaline phosphatase (FastAP, Fermentas, Glen Burnie, Md.) prior to kinasing.

For each assay, the aptamer was thermally equilibrated in tissue culture grade DPBS containing $Mg^{2+}$ and $Ca^{2+}$ (Invitrogen) by heating at 70° C. for 3 minutes followed by incubation at room temperature for 15 minutes. Ten fmoles of radiolabeled aptamer was combined with varying concentrations of protein in a total volume of 50 μL in DPBS. Binding was allowed to come to equilibrium for 30 minutes at room temperature, and bound species were partitioned from unbound species by passing through nitrocellulose and nylon filters under vacuum followed by three successive washes with 500 μL DPBS. Filters were exposed to phosphor screens overnight which were then imaged using a Storm Molecular Imager Phosphorimager (GE Healthcare, Piscataway, N.J.). The fraction of bound aptamer was determined using the ImageQuant software. Kinetic constants were determined by plotting the fraction of bound aptamer against concentration of hTfR, and data was fit to equation 1.

$$f=FA/(Kd+A) \qquad\text{Eq. 1}$$

where f=fraction of bound aptamer, F=maximum fraction of bound aptamer, A=concentration of human transferring receptor and Kd=affinity dissociation constant.

For determination of apparent binding constants by flow cytometry, 100,000 Jurkat cells were incubated with increasing concentrations of AF488-labeled c2.min in RPMI-1640 supplemented with 10% FBS and 1 mg/mL tRNA and ssDNA in 50 μL. Following a 1 hour incubation at 37° C., the cells were washed twice with 1 mL FACS buffer and then resuspended in 500 μL FACS buffer containing 7AAD to exclude dead cells in the analysis. The apparent binding constant was determined from a fit of the mean fluorescence versus the aptamer concentration using the Eq. 1 above.

Transferrin competition binding assays. Assays were performed by flow cytometry on Jurkat cells. Aptamers were thermally equilibrated in tissue culture grade DPBS containing $Mg^{2+}$ and $Ca^{2+}$ by heating at 70° C. for 3 minutes followed by incubation at room temperature for 15 minutes prior to addition to cells. For each reaction 105 cells were pre-blocked by incubated in 50 μL RPMI containing 10% FBS and 1 mg/ml ssDNA and tRNA at 37° C. for 15 minutes prior the addition of 100 nM labeled aptamer (c2minAF488 or cntrl.36AF488) or 100 nM labeled iron loaded transferrin (Dy488-Tf; Jackson labs,) and unlabeled competitor (25 μM, 2.5 μM, 250 nM, 25 nM, or 2.5 nM) in a final volume of 100 μL RPMI containing 10% FBS and 0.5 mg/ml ssDNA and tRNA. Cells were incubated at 37° C. for 1 hr in 96 well tissue culture plates after which cells were washed three times with 1 mL FACS buffer before being resuspended in 500 μL FACS buffer containing 2 μg/mL 7-aminoactinomycin D stain (7AAD) to exclude dead cells in the analysis. Data shown are the average of two independent trials. To ensure iron loading of the labeled transferrin, similar experiments were performed using Dy488-transferrin which had been pretreated by incubation in 400 ug/mL ferric ammonium citrate 10 mM NaHCO3/20 mM HEPES pH 7.7 for 10 minutes followed by desalting [50]. Similar results were observed (data not shown).

Liposome preparation: SNALPs were prepared using the spontaneous vesicle formation by ethanol dilution method [22]. 1,2-Distearoyl-sn-glycero-3-phosphocoline (DSPC), cholesterol, and 1,2-distearoyl-sn-glycero-3-phosphoethanolamine-N-[maleimide(polyethylene glycol)-2000] (DSPE-PEG-Mal) were purchased from Avanti Polar Lipids (Alabaster, Ala.). 1,2-dilinoleyloxy-N,N-dimethyl-3-aminopropane (DLinDMA) was synthesized following the method described by Heyes et al. [24]. siRNA was purchased from Integrated DNA Technologies (Coralville, Iowa).

A 90% vol/vol ethanol solution was prepared containing 10 μmole of total lipid consisting of DSPC/DLinDMA/Cholesterol/DSPE-PEG-Mal (10:40:48:2 mol %). A second solution of equal volume was prepared containing siRNA at a 1:10 molar ratio of Cy5-labeled siRNA to unlabeled siRNA in 20 mM citrate buffer pH 5.0. The amount of anti-GFP or anti-Lamin A/C siRNA added maintained a 2:1 (+/−) charge ratio based on the molar amounts of negatively charged siRNA and positively charged DLinDMA. Both solutions were heated to 37° C. prior to vesicle formation. The siRNA solution was then added to the lipid solution with rapid mixing. The final mixture was diluted with an equal volume of 20 mM citrate pH 6.0 containing 300 mM NaCl and mixed well by rapid pipetting. The resulting mixture was incubated at 37° C. for 30 minutes followed by dialysis with a 10 kDa membrane into PBS, pH 8.0 with 1 mM EDTA overnight. siRNA encapsulation efficiency typically exceeded 90% and was determined using Quant-iT RiboGreen (Invitrogen) as previously described [24] or by gel electrophoresis as described below.

Thiol-modified aptamers were reduced prior to SNALP conjugation by adding TCEP at a final concentration of 20 mM, heating at 70° C. for 3 minutes, and incubating at room temperature for 2 hours. TCEP was removed by passing the sample through a Micro Bio-Spin 6 column (BioRad). After dialysis, thiol-modified aptamers were added to the liposomes at a final concentration of 1.5 μM and incubated for 4 hours at 4° C. Free maleimide groups were quenched the day after aptamer conjugation with 1 mM β-mercaptoethanol (BME) and incubated at room temperature for 3 hours. SNALPs used for transfection purposes were BME-quenched (non-targeted with no aptamer), cntrl.36-conjugated (non-targeted with a conjugated control aptamer), and c2-conjugated (targeted).

Liposome characterization: Particle size distribution was assessed by dynamic light scattering (DynaPro Plate Reader, Wyatt Technology). SNALPs were diluted 1:40 in PBS and analyzed in a 384 well plate after removing bubbles by centrifugation at 1000 g for 3 minutes.

Aptamer conjugation and siRNA encapsulation were analyzed by running each sample on a denaturing (7 M urea) 20% acrylamide gel. Samples were diluted 1:1 in 7 M urea loading buffer and subsequently loaded on the gel without heating. Under these conditions the liposomes remained intact and trapped in the well while any unencapsulated siRNA or unconjugated aptamer ran into the gel. Gels were stained with SYBR Gold and imaged on a Storm 840 phosphorimager (GE Health Sciences). The amount of free aptamer and siRNA was determined by comparison to aptamer or siRNA standard curve. Aptamer functionalized and non-functionalized liposomes were stable for at least one week when stored at 4° C.

The number of aptamers per liposome was estimated based on the observed conjugation efficiency and the concentration of liposomes. Liposome concentration was estimated based on the average diameter of these liposomes (~180 nm), the lipid surface area for packing of a phospholipid, 0.6 nm2 and by assuming that the liposomes are unilamiellar and have spherical geometry [51].

Cell Transfection: HeLa-EGFP cells (20,000 cells/well) were seeded in a 24-well plate in DMEM/High Glucose culture medium supplemented with 5% FBS and antibiotics (D5 media). Twenty-four hours later, D5 media was replaced with D5 supplemented with 10 mg/ml ssDNA in DPBS and 10 mg/ml tRNA in DPBS, as blocking agents. BME-quenched, cntrl.36 non-targeted- or c2 targeted-SNALPs containing either GFP or LaminA/C siRNA were added to cells at a final siRNA concentration in each well of 200 nM and cultured for 24 hours at 37° C. As a positive control, cells were transfected with either 7.5 ng GFP or 7.5 ng LaminA/C siRNA and 3 μl HiPerFect Transfection Reagent (QIAGEN) following the manufacturer's protocol. As a negative control, 3 μl HiPerFect in 100 μl Opti-MEM was added to cells growing in 500 μl D5. After a 24 hour incubation with liposomes or transfection reagent, all media was replaced with fresh D5 media and cells were further incubated for 24 hours before assaying.

Flow Cytometry & RNA Isolation: Transfected cells were washed with PBS and trypsinized. Half of the cells in each sample were centrifuged at 300 g for 3 minutes and resuspended in flow cytometry buffer consisting of HBSS with 1% bovine serum albumin and 0.1% sodium azide. Bisbenzimide was added to the buffer to assess cell viability. These samples were analyzed for knockdown of GFP expression and uptake of Cy5-siRNA on a Sony iCyt Eclipse Analyzer. The second half of each sample was passed through a QIAshredder cell homogenizer (Qiagen, Valencia, Calif.). Total cell RNA for each sample was isolated from the cell lysate according to Qiagen's RNAeasy Plus Mini Kit protocol.

Real Time PCR: cDNA synthesis was performed by first heating the following components to 70° C. for 3 minutes: 100 ng of total RNA isolated as described above, 25 ng of random hexamer primers (Invitrogen), and 2 μl of 5× First Strand RT buffer (Invitrogen). Mixtures were cooled to 4° C. and 2 μl of 4 mM dNTP mix, 1 μl of 0.1 M DTT and 1 μl of Moloney murine leukemia virus reverse transcriptase (Invitrogen) were added to each mixture. Distilled water was added to each sample to make 10 μl final volume reactions. Samples were heated to 37° C. for 50 minutes followed by a 15 minute incubation at 75° C.

Expression levels of GFP mRNA and LaminA/C mRNA were analyzed by quantitative real time PCR on an Applied Biosystems 7300 Real Time PCR machine using TaqMan Univeral Master Mix II (Invitrogen) and specific primer sets. GFP expression was measured using the following primers: GFP-For 5'GACAACCACTACCTGAGCAC (SEQ ID NO:20), GFP-Rev 5'CAGGACCATGTGATCGCG (SEQ ID NO:21), and GFP-probe 5'FAM-CCTGAGCAGCAAAGAC-CCCAACGAGAA-IBFQ (SEQ ID NO:22). LaminA/C expression was measured using the following primers: Lam-For 5' ATGATCGCTTGGCGGTCTAC (SEQ ID NO:23), Lam-Rev 5', GCCCTGCGTTCTCCGTTT (SEQ ID NO:24) and Lam-probe 5' FAM-TCGACCGTGTGCGCTCGCTG-IBFQ (SEQ ID NO:25). RPLP0 expression was used as a standard control with primers: RPLP0-For 5'GGCGAC-CTGGAAGTCCAACT (SEQ ID NO:26), RPLP0-Rev 5'CCATCAGCACCACAGCCTTC (SEQ ID NO:27) and RPLP0-probe 5'FAM-ATCTGCTGCATCTGCTTGGAGC-CCA-IBFQ (SEQ ID NO:28) [52]. Reverse transcription reactions were diluted 1:40 and 10 µl of each sample was used in each 25 µl quantitative real time PCR reaction according to the TaqMan Universal Master Mix II protocol. Each sample was analyzed in triplicate.

Interferon Response: HeLa-EGFP cells were transfected, total RNA was isolated, and cDNA was synthesized as described above. As a positive control, HeLa-EGFP cells were transfected with 100 ng of Poly(I:C) complexed with 3 µl HiPerFect in 100 µl Opti-MEM and incubated for 24 hours at 37° C. RNA isolation and cDNA synthesis were then carried out as described above. Expression levels of interferon-β, CDKL2, and OAS1 were quantified with real time PCR as described above using Power SYBR Green Master Mix (Invitrogen) and specific primer sets: IFNB-F or 5'AGACTTACAGGTTACCTCCGAA (SEQ ID NO:29), IFNB-Rev 5'CAGTACATTCGCCATCAGTCA (SEQ ID NO:30), OAS1-For 5'CGAGGGAGCATGAAAACA-CATTT (SEQ ID NO:31), OAS1-Rev 5'GCAGAGTT-GCTGGTAGTTTATGAC (SEQ ID NO:32), CDKL2-For 5'GCCTCCTTGGGTTCGTCTATAA (SEQ ID NO:33), CDKL2-Rev 5'CTCAGGGCCCGCTCATAGTA (SEQ ID NO:34). RPLP0 was used for normalization purposes. Each sample was analyzed in triplicate.

Example 3

New World hemorrhagic fever arenaviruses utilize the human transferrin receptor (hTfR) to enter and infect cells. Antibodies that target the apical region of this receptor have been shown to block viral entry, inhibiting infection (53, 54). The ability of our anti-hTfR aptamers to block infection of U2OS cells by recombinant VSV-GFP (vesicular stomatitis virus expressing GFP) bearing either the surface glycoprotein from Junin virus, the causative agent of Argentine hemorrhagic fever, or Machupo virus, the causative agent of Bolivian hemorrhagic fever, was assessed. Anti-transferrin receptor aptamers (C2 minimized (SEQ ID NO:50) and Waz (GGGUUCUACGAUAAACGGUUAAUGAUCAGC-UUAUGGCUGGCAGUUCCC (SEQ ID NO:51) having a 3' inverted thymidine and all G and A residues being 2'OH and all C and U residues being 2'F), a non-targeting aptamer control (C36), and free streptavidin (SA) were added individually, as well as a multimeric construct (Waz₄) which was prepared by pre-complexing biotinylated Waz with streptavidin at a ratio of 4:1. Samples had a final aptamer concentration of 1 uM or 250 nM SA and were pre-incubated with cells for 10 minutes at 37° C. before infection with either VSV-Junin or VSV-Machupo as indicated at an MOI of ~0.1. Cells were incubated overnight to allow the infection to proceed and then imaged for expression of GFP, an indicator of viral infection. The total number of infected cells were determined by microscopic analysis. Under these conditions treatment with Waz, or Waz₄ resulted in significant inhibition of viral infection with both VSV-Junin and VSV-Machupo with a greater inhibitory effect observed for Waz₄. This enhanced efficacy is likely due to increased affinity of this multimerized molecule which is achieved through avidity effects. C2 minimized, showed inhibition of VSV-Machupo but not VSV-Junin, while the controls, C36 and SA had no affect on infection. Similarly when experiments were performed with VSV-G, which bears the native VSV surface glycoprotein, no inhibition was observed (see FIG. 8).

TABLE II

Further transferrin receptor aptamer sequences related to 36i and Waz. Recovered from round 9 (R9), round 10 (R10) or from a doped reselection (Dv3R4). (SEQ ID NOS: 52-60, respectively, top to bottom).

| Name | Sequence | Repeat # | Activity |
|------|----------|----------|----------|
| Waz-like (R10) | UGGUUCUACGAUAAACGGUUAAUGAUC AGCUUAUGGCUGGCAGUUCCU | 51 | ++ |
| R10-32 | UGGUUCUACGAUAAACGGUUAAUGAUC AGCUUAUGACUGGCAGUUCCU | 4 | |
| R10-15 | UGAUUGUACGAUAAACGGUUAAUGAUC AGCUUAUGGAUGGCAGUUCCU | 1 | |
| R10-12 | UGGUUCUACGAUAAACGGUUAAUGGUC AGCUUAUGGCUGGCAGUUCCU | 1 | |
| R10-36 | UGGUUCUACGAUAAACGGUUAAUGACC AGCUUAUGGCUGGCAGUUCCU | 1 | ++ |
| R9-03 | UGGUUCUACGAUAAACGGUUAAUGAUC AGCUUAUGGCCGGCAGUUCCU | 2 | |
| Dv3R4-12 | GGGUUCUACGAUAAACGGUUAAUGACC AGCUUAUGACUGGCAGUUCCC | 1 | +/- |
| Dv3R4-20 | GGGUUCUACGACAAACGGUUAAUGAUC AGCUUAUGGCUGGCAGUUCCC | 1 | + |
| Dv3R4-22 | GGGUUUUACGAUAAACGGUUAAUGAUC AGCUUAAGACUGGCAAUUCCC | 1 | ++ |

REFERENCES

1. Daniels T R, Delgado T, Helguera G, Penichet M L (2006). The transferrin receptor part II: targeted delivery of therapeutic agents into cancer cells. *Clin Immunol* 121: 159-176.
2. Daniels T R, Delgado T, Rodriguez J A, Helguera G, Penichet M L (2006). The transferrin receptor part I: Biology and targeting with cytotoxic antibodies for the treatment of cancer. *Clin Immunol* 121: 144-158.
3. Jones A R, Shusta E V (2007). Blood-brain barrier transport of therapeutics via receptor-mediation. *Pharm Res* 24: 1759-1771.
4. Head J F, Wang F, Elliott R L (1997). Antineoplastic drugs that interfere with iron metabolism in cancer cells. *Adv Enzyme Regul* 37: 147-169.
5. Laske D W, et al. (1997). Intraventricular immunotoxin therapy for leptomeningeal neoplasia. *Neurosurgery* 41: 1039-1049; discussion 1049-1051.
6. Laske D W, Youle R J, Oldfield E H (1997). Tumor regression with regional distribution of the targeted toxin TF-CRM107 in patients with malignant brain tumors. *Nat Med* 3: 1362-1368.
7. Weaver M, Laske D W (2003). Transferrin receptor ligand-targeted toxin conjugate (Tf-CRM107) for therapy of malignant gliomas. *J Neurooncol* 65: 3-13.
8. Mendonca L S, Firmino F, Moreira J N, Pedroso de Lima M C, Simoes S (2010). Transferrin receptor-targeted liposomes encapsulating anti-BCR-ABL siRNA or asODN for chronic myeloid leukemia treatment. *Bioconjug Chem* 21: 157-168.
9. Sahoo S K, Ma W, Labhasetwar V (2004). Efficacy of transferrin-conjugated paclitaxel-loaded nanoparticles in a murine model of prostate cancer. *Int J Cancer* 112: 335-340.
10. Matsumura Y, Maeda H (1986). A new concept for macromolecular therapeutics in cancer chemotherapy: mechanism of tumoritropic accumulation of proteins and the antitumor agent smancs. *Cancer Res* 46: 6387-6392.
11. Bartlett D W, Su H, Hildebrandt I J, Weber W A, Davis M E (2007). Impact of tumor-specific targeting on the biodistribution and efficacy of siRNA nanoparticles measured by multimodality in vivo imaging. *Proc Natl Acad Sci USA* 104: 15549-15554.
12. Engler J A, Lee J H, Collawn J F, Moore B A (2001). Receptor mediated uptake of peptides that bind the human transferrin receptor. *European Journal of Biochemistry* 268: 2004-2012.
13. Chen C H B, et al. (2008). Aptamer-based endocytosis of a lysosomal enzyme. *P Natl Acad Sci USA* 105: 15908-15913.
14. Magalhaes M L, et al. (2012). A General RNA Motif for Cellular Transfection. *Mol Ther*.
15. Padilla R, Sousa R (1995). Mutant T7 Rna-Polymerase as a DNA-Polymerase. *Embo Journal* 14: 4609-4621.
16. Padilla R, Sousa R (1999). Efficient synthesis of nucleic acids heavily modified with non-canonical ribose 2'-groups using a mutant T7 RNA polymerase (RNAP). *Nucleic Acids Res* 27: 1561-1563.
17. Pieken W A, Olsen D B, Benseler F, Aurup H, Eckstein F (1991). Kinetic characterization of ribonuclease-resistant 2'-modified hammerhead ribozymes. *Science* 253: 314-317.
18. Schmid S L, Carter L L (1990). Atp Is Required for Receptor-Mediated Endocytosis in Intact-Cells. *J Cell Biol* 111: 2307-2318.
19. Ritchie R F, Palomaki G E, Neveux L M, Navolotskaia O, Ledue T B, Craig W Y (2002). Reference distributions for serum iron and transferrin saturation: a practical, simple, and clinically relevant approach in a large cohort. *J Clin Lab Anal* 16: 237-245.
20. Isselbacher K J, Braunwald E, Wilson J D, Martin J B, Fauci A S, Kasper D L (eds) (1994). *Harrison's Principles of Internal Medicine*, 13th Ed. McGraw-Hill: New York.
21. Young S P, Bomford A, Williams R (1984). The effect of the iron saturation of transferrin on its binding and uptake by rabbit reticulocytes. *Biochem J* 219: 505-510.
22. Jeffs L B, Palmer L R, Ambegia E G, Giesbrecht C, Ewanick S, MacLachlan I (2005). A scalable, extrusion-free method for efficient liposomal encapsulation of plasmid DNA. *Pharmaceutical Research* 22: 362-372.
23. Zimmermann T S, et al. (2006). RNAi-mediated gene silencing in non-human primates. *Nature* 441: 111-114.
24. Heyes J, Palmer L, Bremner K, MacLachlan I (2005). Cationic lipid saturation influences intracellular delivery of encapsulated nucleic acids. *J Control Release* 107: 276-287.
25. Whitehead K A, Langer R, Anderson D G (2009). Knocking down barriers: advances in siRNA delivery. *Nat Rev Drug Discov* 8: 129-138.
26. Zhou J, Rossi J J (2011). Cell-specific aptamer-mediated targeted drug delivery. *Oligonucleotides* 21: 1-10.
27. Dua P, Kim S, Lee D K (2011). Nucleic acid aptamers targeting cell-surface proteins. *Methods* 54: 215-225.
28. Davis M E (2009). The first targeted delivery of siRNA in humans via a self-assembling, cyclodextrin polymer-based nanoparticle: from concept to clinic. *Mol Pharm* 6: 659-668.
29. Davis M E, et al. (2010). Evidence of RNAi in humans from systemically administered siRNA via targeted nanoparticles. *Nature* 464: 1067-1070.
30. Calando P. Safety Study of CALAA-01 to Treat Solid Tumor Cancers. *In: ClinicalTrialsgov [Internet] Bethesda (MD): National Library of Medicine (US)* 20111006 Available from: URL of the record NLM Identifier: NCT00689065.
31. Yu Y J, et al. (2011). Boosting brain uptake of a therapeutic antibody by reducing its affinity for a transcytosis target. *Sci Transl Med* 3: 84ra44.
32. Ni X, et al. (2011). Prostate-targeted radiosensitization via aptamer-shRNA chimeras in human tumor xenografts. *J Clin Invest* 121: 2383-2390.
33. Zhou J, et al. (2009). Selection, characterization and application of new RNA HIV gp 120 aptamers for facile delivery of Dicer substrate siRNAs into HIV infected cells. *Nucleic Acids Res* 37: 3094-3109.
34. Zhou J, Li H, Li S, Zaia J, Rossi J J (2008). Novel dual inhibitory function aptamer-siRNA delivery system for HIV-1 therapy. *Mol Ther* 16: 1481-1489.
35. Wheeler L A, et al. (2011). Inhibition of HIV transmission in human cervicovaginal explants and humanized mice using CD4 aptamer-siRNA chimeras. *J Clin Invest* 121: 2401-2412.
36. McNamara J O, 2nd, et al. (2006). Cell type-specific delivery of siRNAs with aptamer-siRNA chimeras. *Nat Biotechnol* 24: 1005-1015.
37. Dassie J P, et al. (2009). Systemic administration of optimized aptamer-siRNA chimeras promotes regression of PSMA-expressing tumors. *Nat Biotechnol* 27: 839-849.
38. Dhar S, Gu F X, Langer R, Farokhzad O C, Lippard S J (2008). Targeted delivery of cisplatin to prostate cancer cells by aptamer functionalized Pt(IV) prodrug-PLGA-PEG nanoparticles. *Proc Natl Acad Sci USA* 105: 17356-17361.
39. Farokhzad O C, et al. (2006). Targeted nanoparticle-aptamer bioconjugates for cancer chemotherapy in vivo. *Proc Natl Acad Sci USA* 103: 6315-6320.
40. Mann A P, et al. (2011). Thioaptamer conjugated liposomes for tumor vasculature targeting. *Oncotarget* 2: 298-304.
41. Kang H, O'Donoghue M B, Liu H, Tan W (2010). A liposome-based nanostructure for aptamer directed delivery. *Chem Commun (Camb)* 46: 249-251.
42. Tan L, Neoh K G, Kang E T, Choe W S, Su X (2011). PEGylated Anti-MUC1 Aptamer-Doxorubicin Complex for Targeted Drug Delivery to MCF7 Breast Cancer Cells. *Macromol Biosci*.
43. Judge A D, et al. (2009). Confirming the RNAi-mediated mechanism of action of siRNA-based cancer therapeutics in mice. *J Clin Invest* 119: 661-673.
44. Corporation T P. Dose Escalation Study to Determine Safety, Pharmacokinetics, and Pharmacodynamics of Intravenous TKM-080301. *In: ClinicalTrialsgov [Internet] Bethesda (MD): National Library of Medicine (US)* 20111006 Available from: URL of the record NLM Identifier: NCT01262235.
45. (NCI) NCI. TKM 080301 for Primary or Secondary Liver Cancer. *In: ClinicalTrialsgov [Internet] Bethesda*

(*MD*): *National Library of Medicine* (*US*) 20111006 *Available from: URL of the record NLM Identifier: NCT*01437007.

46. Akinc A, et al. (2010). Targeted Delivery of RNAi Therapeutics With Endogenous and Exogenous Ligand-Based Mechanisms. *Molecular Therapy* 18: 1357-1364.
47. Jeffs L B, Palmer L R, Ambegia E G, Giesbrecht C, Ewanick S, MacLachlan I (2005). A scalable, extrusion-free method for efficient liposomal encapsulation of plasmid DNA. *Pharm Res* 22: 362-372.
48. Hall B, Micheletti J M, Satya P, Ogle K, Pollard J, Ellington A D (2009). Design, synthesis, and amplification of DNA pools for in vitro selection. *Curr Protoc Nucleic Acid Chem* Chapter 9: Unit 9 2.
49. Wong I, Lohman T M (1993). A double-filter method for nitrocellulose-filter binding: application to protein-nucleic acid interactions. *Proc Natl Acad Sci USA* 90: 5428-5432.
50. McGraw T E, Subtil A (2001). Endocytosis: biochemical analyses. *Curr Protoc Cell Biol* Chapter 15: Unit 15 13.
51. Reulen S W A, Brusselaars W W T, Langereis S, Mulder W J M, Breurken M, Merkx M (2007). Protein-liposome conjugates using cysteine-lipids and native chemical ligation. *Bioconjugate Chem* 18: 590-596.
52. Collingwood M A, et al. (2008). Chemical modification patterns compatible with high potency Dicer-substrate small interfering RNAs. *Oligonucleotides* 18: 187-199.
53. Radoshitzky, S. R. et al. Transferrin receptor 1 is a cellular receptor for New World haemorrhagic fever arenaviruses. Nature 446, 92-96 (2007).
54. Helguera, G. et al. An antibody recognizing the apical domain of human transferrin receptor 1 efficiently inhibits the entry of all New World hemorrhagic fever arenaviruses. Journal of Virology (2012). doi:10.1128/JVI.06397-11.

What is claimed is:

1. An isolated ribonucleic acid aptamer comprising SEQ ID NO:1, 2, 3, 5, 10, 51, 52, 56, 59 or 60.

2. The isolated aptamer of claim 1, wherein one or more pyrimidine residues thereof comprise a 2' F group.

3. The isolated aptamer of claim 1, wherein one or more purine residues thereof comprise a 2' F group.

4. The isolated aptamer of claim 1, wherein one or more purine residues thereof comprise a 2' OMe group.

5. The isolated aptamer of claim 1, wherein all the pyrimidine residues thereof comprise a 2' F group.

6. The isolated aptamer of claim 1, wherein all the purine residues thereof comprise a 2' H group or a 2' OMe group.

7. The isolated aptamer of claim 1, comprising SEQ ID NO:10 or 51.

8. The isolated aptamer of claim 1, which binds a human transferrin receptor.

9. The isolated aptamer of claim 1, wherein the aptamer does not compete for binding with human transferrin to a human transferrin receptor.

10. A composition, comprising the aptamer of claim 1 conjugated to one of an oligonucleotide, a small organic molecule of less than 2000 daltons, a liposome or a nanoparticle.

11. A method of delivering a molecular entity to a receptor-expressing cell in a subject comprising administering to the subject a composition comprising a ribonucleic acid aptamer comprising SEQ ID NO:1, 2, 3, 5, 10, 50, 51, 52, 56, 59 or 60, wherein the molecular entity is conjugated to the aptamer or contained in a liposome attached to the aptamer, so as to thereby deliver the molecular entity to a receptor-expressing cell.

12. A method of treating a subject exposed to a New World arenavirus which is a VSV-Junin or a VSV-Machupo comprising administering to the subject an amount of (i) composition comprising SEQ ID NO:51 to treat a subject exposed to VSV-Junin or to VSV-Machupo, or (ii) a composition comprising SEQ ID NO:50 to treat a subject exposed to VSV-Machupo.

13. The method of claim 12, wherein one or more pyrimidine residues of SEQ ID NO:50 or SEQ ID NO:51 comprise a 2' F group, and/or wherein one or more purine residues thereof comprise a 2' F group, and/or wherein one or more purine residues thereof comprise a 2' OMe group, and/or wherein all the pyrimidine residues thereof comprise a 2' F group, and/or wherein all the purine residues thereof comprise a 2' H group or a 2' OMe group.

14. The method of claim 12, wherein SEQ ID NO:50 or SEQ ID NO:51 comprises a 3' inverted deoxy-thymidine.

15. The method of claim 12, wherein all G and A residues of SEQ ID NO:50 or SEQ ID NO:51 comprise a 2'OH group.

16. The method of claim 12, wherein all C and U residues of SEQ ID NO:50 or SEQ ID NO:51 comprise a 2'F group.

17. The method of claim 11, wherein the ribonucleic acid aptamer comprises SEQ ID NO:1, 2, 3, 5, 10, 51, 52, 56, 59 or 60.

* * * * *

SEQUENCE LISTING

```
<160> NUMBER OF SEQ ID NOS: 67

<210> SEQ ID NO 1
<211> LENGTH: 93
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 1
gggaggugaa ugguucuacg auaaacgguu aaugaccagc uuauggcugg caguuccuau      60
agcaccaacu acaugcgaga ugaccacgua aug                                   93

<210> SEQ ID NO 2
<211> LENGTH: 64
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 2
gggugaaugg uucuacgaua aacgguuaau gaccagcuua uggcuggcag uuccuauagc      60
accc                                                                   64

<210> SEQ ID NO 3
<211> LENGTH: 53
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 3
gggaguucua cgauaaacgg uuaaugacca gcuuauggcu ggcaguuccu ccc              53

<210> SEQ ID NO 4
<211> LENGTH: 44
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 4
gggaguucua guuaaugacc agcuuauggc uggcaguucc uccc                        44

<210> SEQ ID NO 5
```

```
<211> LENGTH: 33
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 5
ggguuaauga ccagcuuaug gcuggcaguu ccc                                    33

<210> SEQ ID NO 6
<211> LENGTH: 66
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 6
gggugaaugg uucuacgaua aacggguuaa ugaccagcuu auggcuggca guucccuaua       60
gcaccc                                                                  66

<210> SEQ ID NO 7
<211> LENGTH: 57
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 7
gggugaaugg uucuacgaua aacgguuaau gaccgaaagg caguuccuau agcaccc          57

<210> SEQ ID NO 8
<211> LENGTH: 56
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 8
gggugaauca uaaacgguua augaccagcu uauggcuggc aguuccuaca gcaccc           56

<210> SEQ ID NO 9
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 9
gggugaaugg uucuacgaua aacggcuuaa uaguugccua uagcaccc                   48

<210> SEQ ID NO 10
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 10
ggguucuacg auaaacgguu aaugaccagc uuauggcugg caguccc                    48

<210> SEQ ID NO 11
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER
```

-continued

<400> SEQUENCE: 11
gggaacuacg auaaacgguu aaugaccagc uuauggcugg caguuccc         48

<210> SEQ ID NO 12
<211> LENGTH: 42
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 12
ggguacgaua aacgguuaau gaccagcuua uggcuggcac cc              42

<210> SEQ ID NO 13
<211> LENGTH: 42
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 13
ggguacgaua aacgguuaag gaccagcuua uggcuggccc cc              42

<210> SEQ ID NO 14
<211> LENGTH: 42
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 14
ggguacgaca aacggucaau gaccagcuua uggcuggcac cc              42

<210> SEQ ID NO 15
<211> LENGTH: 121
<212> TYPE: DNA
<213> ORGANISM: ARTIFICIAL SEQUENCE
<220> FEATURE:
<223> OTHER INFORMATION: ENCODING PORTION OF HUMAN TRANSFERRIN RECEPTOR
<220> FEATURE:
<221> NAME/KEY: misc_feature
<222> LOCATION: (23)..(72)
<223> OTHER INFORMATION: n = A, T, G or C

<400> SEQUENCE: 15
gggaggtgaa tggttctacg atnnnnnnnn nnnnnnnnnn nnnnnnnnnn nnnnnnnnnn    60
nnnnnnnnnn nnttacatgc gagatgacca cgtaattgaa ttaaatgccc gccatgacca   120
g                                                                  121

<210> SEQ ID NO 16
<211> LENGTH: 24
<212> TYPE: DNA
<213> ORGANISM: ARTIFICIAL SEQUENCE
<220> FEATURE:
<223> OTHER INFORMATION: PRIMER DIRECTED TO TRANSFERRIN

<400> SEQUENCE: 16
ctggtcatgg cgggcattta attc                                          24

<210> SEQ ID NO 17
<211> LENGTH: 24
<212> TYPE: DNA
<213> ORGANISM: ARTIFICIAL SEQUENCE
<220> FEATURE:

<223> OTHER INFORMATION: RNA aptamer constant region

<400> SEQUENCE: 17
gaattaaatg cccgccatga ccag                24

<210> SEQ ID NO 18
<211> LENGTH: 44
<212> TYPE: DNA
<213> ORGANISM: ARTIFICIAL SEQUENCE
<220> FEATURE:
<223> OTHER INFORMATION: ARTIFICIAL APTAMER DIRECTED TO HUMAN
      TRANSFERRIN

<400> SEQUENCE: 18
gggggaucaa uccaagggac ccggaaacgc ucccuuacac ccct           44

<210> SEQ ID NO 19
<211> LENGTH: 37
<212> TYPE: DNA
<213> ORGANISM: ARTIFICIAL SEQUENCE
<220> FEATURE:
<223> OTHER INFORMATION: ARTIFICIAL APTAMER DIRECTED TO HUMAN
      TRANSFERRIN

<400> SEQUENCE: 19
ggcguaguga uuaugaaucg ugugcuaaua cacgcct              37

<210> SEQ ID NO 20
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN TRANSFERRIN

<400> SEQUENCE: 20
gacaaccact acctgagcac                 20

<210> SEQ ID NO 21
<211> LENGTH: 18
<212> TYPE: DNA
<213> ORGANISM: ARTIFICIAL SEQUENCE
<220> FEATURE:
<223> OTHER INFORMATION: PRIMER DIRECTED TO HUMAN TRANSFERRIN

<400> SEQUENCE: 21
caggaccatg tgatcgcg                  18

<210> SEQ ID NO 22
<211> LENGTH: 24
<212> TYPE: DNA
<213> ORGANISM: ARTIFICIAL SEQUENCE
<220> FEATURE:
<223> OTHER INFORMATION: PRIMER DIRECTED TO HUMAN TRANSFERRIN

<400> SEQUENCE: 22
cctgagcaaa gaccccaacg agaa               24

<210> SEQ ID NO 23
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN TRANSFERRIN

<400> SEQUENCE: 23
atgatcgctt ggcggtctac                 20

```
<210> SEQ ID NO 24
<211> LENGTH: 18
<212> TYPE: DNA
<213> ORGANISM: ARTIFICIAL SEQUENCE
<220> FEATURE:
<223> OTHER INFORMATION: PRIMER DIRECTED TO HUMAN TRANSFERRIN

<400> SEQUENCE: 24
gccctgcgtt ctccgttt                                                 18

<210> SEQ ID NO 25
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN TRANSFERRIN

<400> SEQUENCE: 25
tcgaccgtgt gcgctcgctg                                               20

<210> SEQ ID NO 26
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN TRANSFERRIN

<400> SEQUENCE: 26
ggcgacctgg aagtccaact                                               20

<210> SEQ ID NO 27
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN TRANSFERRIN

<400> SEQUENCE: 27
ccatcagcac cacagccttc                                               20

<210> SEQ ID NO 28
<211> LENGTH: 25
<212> TYPE: DNA
<213> ORGANISM: ARTIFICIAL SEQUENCE
<220> FEATURE:
<223> OTHER INFORMATION: PRIMER DIRECTED TO HUMAN TRANSFERRIN

<400> SEQUENCE: 28
atctgctgca tctgcttgga gccca                                         25

<210> SEQ ID NO 29
<211> LENGTH: 50
<212> TYPE: RNA
<213> ORGANISM: ARTIFICIAL SEQUENCE
<220> FEATURE:
<223> OTHER INFORMATION: ARTIFICIAL PRIMER

<400> SEQUENCE: 29
ucaaacaucu cacagaucaa uccaagggac cucguuaaag gacgacuccc              50

<210> SEQ ID NO 30
<211> LENGTH: 51
<212> TYPE: RNA
<213> ORGANISM: ARTIFICIAL SEQUENCE
<220> FEATURE:
```

```
<223> OTHER INFORMATION: ARTIFICIAL APTAMER

<400> SEQUENCE: 30
uagguuagcc gcagaucacu acaaagcccc uagagcacau gcuccaccgc u          51

<210> SEQ ID NO 31
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 31
cauuacggcu accccguguaa acgucagcca aaguagacca aaagucag             48

<210> SEQ ID NO 32
<211> LENGTH: 50
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 32
acgcauggca ggaagcaugu uaucccuaa gaauccgcaa ucgcucguaa             50

<210> SEQ ID NO 33
<211> LENGTH: 50
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 33
cagaugacaa agcgcaucag aagaauaaag ugagauaaag ugugagaggg            50

<210> SEQ ID NO 34
<211> LENGTH: 50
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 34
uuugugaccu ggucagggag uugaagggguc gcucuuuuga aaagccuugg           50

<210> SEQ ID NO 35
<211> LENGTH: 52
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 35
ccgcgaaacu uaaaaaaaac gacaaacgcg ugagccgggc aagguaggua uu         52

<210> SEQ ID NO 36
<211> LENGTH: 66
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 36
aguagcuuga aaucagaaaa ccgacgaaac aaaaaauaug auuuagcaag gaugaccacg 60
uaauug                                                            66
```

```
<210> SEQ ID NO 37
<211> LENGTH: 49
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 37
agggugaaau ugcgagcguu gcccaacuuu auaaguuggu gaauagcca            49

<210> SEQ ID NO 38
<211> LENGTH: 50
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 38
acaaguaucg guuuuacaau acagacguac agugcgauag ccaagcggaa           50

<210> SEQ ID NO 39
<211> LENGTH: 92
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 39
gggaggugaa uggucuacga uucaaacauc ucacagauca auccaaggga ccucguuaaa   60
ggacgacucc cuuacaugcg agaugaccac gu                              92

<210> SEQ ID NO 40
<211> LENGTH: 96
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 40 gggaggugaaугguucuacg auuaggguag ccgcagauca cuacaaagcc ccuagagcac   60
augcuccacc gcuuuacaug ccgagaugac caccgu                          96

<210> SEQ ID NO 41
<211> LENGTH: 91
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 41
gggaggugaa ugguucuacg aucauuacgg cuaccccgug uaacgucagc caaaguagac   60
caaaagucag uuacaugcga gaugaccacg u                               91

<210> SEQ ID NO 42
<211> LENGTH: 30
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 42
ggggaccucg uuaaaggacg acuccccuuu                                 30
```

```
<210> SEQ ID NO 43
<211> LENGTH: 64
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 43
gggagcaucu cacagaucaa uccaagggac cucguuaaag gacgacyccc uuacaugcga      60
gaug                                                                  64

<210> SEQ ID NO 44
<211> LENGTH: 35
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 44
gggaagggac cucguuaaag gacgacuccc uuaca                                 35

<210> SEQ ID NO 45
<211> LENGTH: 52
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 45
gggagcaucu cacagaucaa uccaagggac cuacucccuu acaugcgaga ug              52

<210> SEQ ID NO 46
<211> LENGTH: 50
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 46
gggagcaucu cacagaucaa uccaagggga aaucccuuac augcgagaug                 50

<210> SEQ ID NO 47
<211> LENGTH: 55
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 47
ggggacagau caauccaagg gaccucguua aaggacgacu cccuuacaug ucccc           55

<210> SEQ ID NO 48
<211> LENGTH: 45
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 48
gggggaucaa uccaagggac cucggaaacg acucccuuac acccc                      45

<210> SEQ ID NO 49
<211> LENGTH: 51
<212> TYPE: RNA
<213> ORGANISM: ARTIFICIAL SEQUENCE
```

```
<220> FEATURE:
<223> OTHER INFORMATION: ARTIFICIAL APTAMER

<400> SEQUENCE: 49
ggggacagau caauuccggc uaccccgugu aacgucuagc cacauguccc c                51

<210> SEQ ID NO 50
<211> LENGTH: 43
<212> TYPE: RNA
<213> ORGANISM: ARTIFICIAL SEQUENCE
<220> FEATURE:
<223> OTHER INFORMATION: ARTIFICIAL APTAMER
<220> FEATURE:
<221> NAME/KEY: misc_feature
<222> LOCATION: (43)..(43)
<223> OTHER INFORMATION: Optionally a 3' inverted deoxy-thymidine is
      attached to this residue

<400> SEQUENCE: 50
gggggaucaa uccaagggac ccggaaacgc ucccuuacac ccc                         43

<210> SEQ ID NO 51
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER
<220> FEATURE:
<221> NAME/KEY: misc_feature
<222> LOCATION: (48)..(48)
<223> OTHER INFORMATION: Optionally a 3' inverted deoxy-thymidine is
      attached to this residue

<400> SEQUENCE: 51
ggguucuacg auaaacgguu aaugaucagc uuauggcugg caguuccc                    48

<210> SEQ ID NO 52
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 52
ugguucuacg auaaacgguu aaugaucagc uuauggcugg caguuccu                    48

<210> SEQ ID NO 53
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 53
ugguucuacg auaaacgguu aaugaucagc uuaugacugg caguuccu                    48

<210> SEQ ID NO 54
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 54
ugauuguacg auaaacgguu aaugaucagc uuauggaugg caguuccu                    48

<210> SEQ ID NO 55
```

```
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 55
ugguucuacg auaaacgguu aauggucagc uuauggcugg caguuccu            48

<210> SEQ ID NO 56
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 56
ugguucuacg auaaacgguu aaugaccsgc uuauggcugg caguuccu            48

<210> SEQ ID NO 57
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 57
ugguucuacg auaaacgguu aaugaucagc uuauggccgg caguuccu            48

<210> SEQ ID NO 58
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 58
ggguucuacg auaaacgguu aaugaccagc uuaugacugg caguuccc            48

<210> SEQ ID NO 59
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 59
ggguucuacg acaaacgguu aaugaucagc uuauggcugg caguuccc            48

<210> SEQ ID NO 60
<211> LENGTH: 48
<212> TYPE: RNA
<213> ORGANISM: ARTIFICIAL SEQUENCE
<220> FEATURE:
<223> OTHER INFORMATION: ARTIFICIAL APTAMER

<400> SEQUENCE: 60
ggguuuuacg auaaacgguu aaugaucagc uuaagacugg caauuccc            48

<210> SEQ ID NO 61
<211> LENGTH: 9
<212> TYPE: RNA
<213> ORGANISM: ARTIFICIAL SEQUENCE
<220> FEATURE:
<223> OTHER INFORMATION: ARTIFICIAL APTAMER
<220> FEATURE:
<221> NAME/KEY: misc_feature
```

```
<222> LOCATION: (6)..(6)
<223> OTHER INFORMATION: Y = U OR C
<220> FEATURE:
<221> NAME/KEY: misc_feature
<222> LOCATION: (8)..(8)
<223> OTHER INFORMATION: M = A OR C

<400> SEQUENCE: 61 gaucayumc                                                                  9

<210> SEQ ID NO 62
<211> LENGTH: 22
<212> TYPE: DNA
<213> ORGANISM: ARTIFICIAL SEQUENCE
<220> FEATURE:
<223> OTHER INFORMATION: PRIMER DIRECTED TO HUMAN INTERFERON

<400> SEQUENCE: 62
agacttacag gttacctccg aa                                                  22

<210> SEQ ID NO 63
<211> LENGTH: 21
<212> TYPE: DNA
<213> ORGANISM: ARTIFICIAL SEQUENCE
<220> FEATURE:
<223> OTHER INFORMATION: PRIMER DIRECTED TO HUMAN INTERFERON

<400> SEQUENCE: 63
cagtacattc gccatcagtc a                                                   21

<210> SEQ ID NO 64
<211> LENGTH: 23
<212> TYPE: DNA
<213> ORGANISM: ARTIFICIAL SEQUENCE
<220> FEATURE:
<223> OTHER INFORMATION: PRIMER DIRECTED TO HUMAN OAS1

<400> SEQUENCE: 64
cgagggagca tgaaaacaca ttt                                                 23

<210> SEQ ID NO 65
<211> LENGTH: 24
<212> TYPE: DNA
<213> ORGANISM: ARTIFICIAL SEQUENCE
<220> FEATURE:
<223> OTHER INFORMATION: PRIMER DIRECTED TO HUMAN OAS1

<400> SEQUENCE: 65
gcagagttgc tggtagttta tgac                                                24

<210> SEQ ID NO 66
<211> LENGTH: 22
<212> TYPE: DNA
<213> ORGANISM: ARTIFICIAL SEQUENCE
<220> FEATURE:
<223> OTHER INFORMATION: PRIMER DIRECTED TO HUMAN CDKL2

<400> SEQUENCE: 66
gcctccttgg gttcgtctat aa                                                  22

<210> SEQ ID NO 67
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CDKL2
```

```
<400> SEQUENCE: 67
ctcagggccc gctcatagta                                          20
```